US008137906B2

(12) United States Patent
Schatz

(10) Patent No.: US 8,137,906 B2
(45) Date of Patent: Mar. 20, 2012

(54) METHOD FOR THE SYNTHESIS OF DNA FRAGMENTS

(75) Inventor: Octavian Schatz, Altomunster (DE)

(73) Assignee: Sloning Biotechnology GmbH, Martinsried (DE)

( * ) Notice: Subject to any disclaimer, the term of this patent is extended or adjusted under 35 U.S.C. 154(b) by 0 days.

(21) Appl. No.: 11/336,198

(22) Filed: Jan. 20, 2006

(65) Prior Publication Data

US 2006/0115850 A1 Jun. 1, 2006

Related U.S. Application Data

(63) Continuation of application No. 10/009,926, filed as application No. PCT/DE00/01863 on Jun. 7, 2000, now abandoned.

(30) Foreign Application Priority Data

Jun. 7, 1999 (DE) .................................. 199 25 862

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl. ......... 435/6; 435/91.1; 536/23.1; 536/24.3; 536/24.33; 536/25.3

(58) Field of Classification Search .............. 435/6, 91.1, 435/183; 436/94; 536/23.1, 24.3, 24.33, 536/25.3, 25.32
See application file for complete search history.

(56) References Cited

U.S. PATENT DOCUMENTS

| | | | |
|---|---|---|---|
| 4,652,639 A | 3/1987 | Stabinsky | |
| 5,093,251 A | 3/1992 | Richards | |
| 5,132,215 A | 7/1992 | Jayaraman | |
| 5,397,698 A | 3/1995 | Goodman et al. | |
| 5,508,169 A | 4/1996 | Deugau et al. | |
| 5,710,000 A | 1/1998 | Sapolsky et al. | |
| 5,770,365 A * | 6/1998 | Lane et al. ............. | 435/6 |
| 5,858,656 A | 1/1999 | Deugau et al. | |
| 5,888,737 A * | 3/1999 | DuBridge et al. ........ | 435/6 |
| 5,981,190 A * | 11/1999 | Israel ..................... | 435/6 |
| 6,110,668 A | 8/2000 | Strizhov | |
| 6,472,184 B1 | 10/2002 | Hegemann | |
| 6,485,944 B1 * | 11/2002 | Church et al. ........... | 435/91.2 |
| 2006/0115850 A1 | 6/2006 | Schatz | |
| 2006/0194202 A1 * | 8/2006 | Schatz et al. ........... | 435/6 |
| 2008/0044862 A1 | 2/2008 | Schatz et al. | |

FOREIGN PATENT DOCUMENTS

| | | |
|---|---|---|
| EP | 0245130 | 11/1987 |
| EP | 0533838 | 3/1993 |
| EP | 1411122 | 4/2004 |
| WO | WO93/19202 | 9/1993 |
| WO | W095/17413 | 6/1995 |
| WO | 9612014 | 4/1996 |
| WO | WO96/12014 | 4/1996 |
| WO | 9815567 | 4/1998 |
| WO | WO98/10095 | 12/1998 |
| WO | W099/47536 | 9/1999 |
| WO | WO01/61036 | 8/2001 |
| WO | WO01/75180 | 10/2001 |
| WO | 0175180 A2 | 11/2001 |

OTHER PUBLICATIONS

Roberts, R.J., and D. Macelis (1999) Rebase—restriction enzymes and methylases. Nucleic Acids Res 27: 312-313.
Xiong et al: "Non-polymerase-cycling-assembly-based chemical gene synthesis: Strategies, methods, and progress", Biotechnology Advances, Elsevier Publishing, Barking, GB, vol. 26, No. 2, Nov. 7, 2007, pp. 121-134, XP022426820.
Eugen Uhlmann: "An alternative approach in gene synthesis: use of long selfpriming oligodeoxynucleotides for the construction of double-stranded DNA", Gene, vol. 71, Nov. 15, 1988, pp. 29-40, XP000941756.
Wlodek Mandecki et al.: "A totally synthetic plasmid for general cloning, gene expression and mutagenesis in *Escherichia coli*", Gene, vol. 94, Sep. 28, 1990, pp. 103-107, XP000941757.
Van Den Brulle, et al.: "A novel solid phase technology for high-throughput gene synthesis", Biotechniques vol. 45, No. 3, 2008, pp. 340-343.
Padgett KA et al.: I"Creating seamless junctions independent of restriction site in PCR cloning", Gene, Elsevier Biomedical Press. Amsterdam, NL, vol . 168, No. 1, Feb. 2, 1996, pp. 31-35, XP004042930.
Kato K: "Description of the Entire MRNA Population by A3'End CDNA Fragment Generated by Class IIS Restriction Enzymes", Nucleic Acids Research, Oxford University, Press, Surrey, GB, vol. 23, No. 18, Sep. 1, 1995, pp. 3685-3690, XP002008304.
Shibata Y et al: Cloning full-length, Cap-Trapper-selected cDNAs by using the single-strand linker ligation method. II, Biotechniques, vol. 30, No. 6, Jun. 2001, pp. 1250-1254, XP002197302.
Unrau Paul et al: "Non-cloning amplification of specific DNA fragments from whole genomic DNA digests using DNA, indexers'", Gene, Elsevier Biomedical Press. Amsterdam, NL, vol. 145, No. 2, 1994, pp. 163-169, XP002149819.
Velculescu VE et al: "Serial Analysis of Gene Expression" Science, American Association for the Advancement of Science US, vol. 270, No. 5235, Oct. 20, 1995, pp. 484-487, XP001024449.

(Continued)

Primary Examiner — Frank W Lu

(57) ABSTRACT

The invention relates to a method that can be carried out in parallel and automated for the production of any nucleic acid, comprising the following steps: a) coupling an oligonucleotide to a solid matrix b) adding an additional oligonucleotide c) ligating the oligonucleotides from steps a) and b) in one orientation d) removing excess reactants and enzymes from the reaction preparation e) cleaving the ligation product from step c) with a restriction enzyme that cleaves outside the recognition sequence, whereby cleavage occurs in the oligonucleotide from step a) or in the oligonucleotide from step b) f) separating the reaction mixture from the lengthened or shortened oligonucleotide from step a) that is obtained in step e) g) repeating steps b) to f) at least once h) successive sequence-independent linkage of the fragments obtained after performing steps a) to g) until the desired product is obtained.

13 Claims, 8 Drawing Sheets

OTHER PUBLICATIONS

Shao-Chi Huang et al., "Binding of biotinylated DNA to Streptavidin-Coated Polystryrene Latex." 222 Analytical Biochemistry (1994) 441-449.

Bolli, et al.; Pyranosyl-RNA:chiroselective self-assembly of base sequences by ligative oligomerization of tetranucleotide-2', 3'-cyclophosphates, 1997, Chern.Biol. 4(4): 309-320.

Hoare & Koshland; A method for the quantitative modification and estimation of carboxylic acid groups in proteins, 1967,1. Biol. Chern. 242(10): 2447-2453.

Sekiya, et al.; Total Synthesis of a tyrosine suppressor tRNA gene. xv. Synthesis of the promoter region, 1979, J. Bioi. Chern. 254(13): 5781-5786.

Sekiya, et al.; Total synthesis of a tyrosine suppressor transfer RNA gene. XVI Enzymatic joinings to form the total 207-base pair-long DNA, 1979,1. Biol. Chern. 254(13): 5787-5801.

Crawford, M., et al., Briefings in Functional Genomics and Proteomics, vol. 2, No. 1, pp. 72-79, Apr. 2003.

* cited by examiner ligation of anchor and fluorescent splinker
(when ends are aligned by hybridization)

bipartite anchor (reconstitution of the Esp3I cleavage site after ligation)

SEQUENCE LISTING

<160> NUMBER OF SEQ ID NOS: 31

<210> SEQ ID NO 1
<211> LENGTH: 26
<212> TYPE: DNA
<213> ORGANISM: Artificial sequence
<220> FEATURE:
<223> OTHER INFORMATION: oligonucleotide

<400> SEQUENCE: 1
gcttcgagac gcgttttcgc gtctcg                                          26

<210> SEQ ID NO 2
<211> LENGTH: 32
<212> TYPE: DNA
<213> ORGANISM: Artificial sequence
<220> FEATURE:
<223> OTHER INFORMATION: oligonucleotide

<400> SEQUENCE: 2
agaatggtct tcgagctttt gctcgaagac ca                                   32

<210> SEQ ID NO 3
<211> LENGTH: 16
<212> TYPE: DNA
<213> ORGANISM: Artificial sequence
<220> FEATURE:
<223> OTHER INFORMATION: oligonucleotide

<400> SEQUENCE: 3

```
cgcggatccg cggcgt                                                     16
```

<210> SEQ ID NO 4
<211> LENGTH: 20
<212> TYPE: DNA
<213> ORGANISM: Artificial sequence
<220> FEATURE:
<223> OTHER INFORMATION: oligonucleotide

<400> SEQUENCE: 4

```
cgagacgccg cggatccgcg                                                 20
```

<210> SEQ ID NO 5
<211> LENGTH: 34
<212> TYPE: DNA
<213> ORGANISM: Artificial sequence
<220> FEATURE:
<223> OTHER INFORMATION: oligonucleotide

<400> SEQUENCE: 5

```
aagcttctgg agaccgcttt tgcggtctcc agaa                                 34
```

<210> SEQ ID NO 6
<211> LENGTH: 20
<212> TYPE: DNA
<213> ORGANISM: Artificial sequence
<220> FEATURE:
<223> OTHER INFORMATION: oligonucleotide

<400> SEQUENCE: 6

```
ctcgaagcgg agaccgccac                                                 20
```

<210> SEQ ID NO 7
<211> LENGTH: 16
<212> TYPE: DNA
<213> ORGANISM: Artificial sequence
<220> FEATURE:
<223> OTHER INFORMATION: oligonucleotide

<400> SEQUENCE: 7

```
gtggcggtct ccgctt                                                     16
```

<210> SEQ ID NO 8
<211> LENGTH: 11
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, t, g, or c

<400> SEQUENCE: 8

```
cgtctcnnnn n                                                          11
```

<210> SEQ ID NO 9
<211> LENGTH: 11
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, t, c or g

<400> SEQUENCE: 9

```
ggtctcnnnn n                                                    11

<210> SEQ ID NO 10
<211> LENGTH: 11
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, t, g, or c

<400> SEQUENCE: 10
ggtctcnnnn n                                                    11

<210> SEQ ID NO 11
<211> LENGTH: 11
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, t, c, or g

<400> SEQUENCE: 11
cgtctcnnnn n                                                    11

<210> SEQ ID NO 12
<211> LENGTH: 12
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(12)
<223> OTHER INFORMATION: n is a, t, c, or g

<400> SEQUENCE: 12
gaagacnnnn nn                                                   12

<210> SEQ ID NO 13
<211> LENGTH: 14
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(14)
<223> OTHER INFORMATION: n is a, t, c, or g

<400> SEQUENCE: 13
acctgcnnnn nnnn                                                 14

<210> SEQ ID NO 14
<211> LENGTH: 14
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(14)
<223> OTHER INFORMATION: n is a, t, c, or g

<400> SEQUENCE: 14
```

```
acctgcnnnn nnnn                                                          14
```

```
<210> SEQ ID NO 15
<211> LENGTH: 12
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(14)
<223> OTHER INFORMATION: n is a, t, c, or g

<400> SEQUENCE: 15
gaagacnnnn nn                                                            12

<210> SEQ ID NO 16
<211> LENGTH: 8
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(8)
<223> OTHER INFORMATION: n is a, t, c, or g

<400> SEQUENCE: 16 gcagtgnn                                                                  8

<210> SEQ ID NO 17
<211> LENGTH: 8
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(8)
<223> OTHER INFORMATION: n is a, c, g, or t

<400> SEQUENCE: 17 gcaatgnn                                                                  8

<210> SEQ ID NO 18
<211> LENGTH: 8
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(8)
<223> OTHER INFORMATION: n is a, t, c, or g

<400> SEQUENCE: 18 gcaatgnn                                                                  8

<210> SEQ ID NO 19
<211> LENGTH: 8
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(8)
<223> OTHER INFORMATION: n is a, t, c, or g

<400> SEQUENCE: 19
```

```
gcagtgnn                                                             8

<210> SEQ ID NO 20
<211> LENGTH: 12
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(12)
<223> OTHER INFORMATION: n is a, t, c, or g

<400> SEQUENCE: 20
gtatccnnnn nn                                                       12

<210> SEQ ID NO 21
<211> LENGTH: 11
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t

<400> SEQUENCE: 21
actgggnnnn n                                                        11

<210> SEQ ID NO 22
<211> LENGTH: 11
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, t, c, or g

<400> SEQUENCE: 22
actgggnnnn n                                                        11

<210> SEQ ID NO 23
<211> LENGTH: 12
<212> TYPE: DNA
<213> ORGANISM: Artificial sequence'
<220> FEATURE:
<223> OTHER INFORMATION: oligonucleotide
<220> FEATURE:
<221> NAME/KEY: misc_feature
<222> LOCATION: (7)..(12)
<223> OTHER INFORMATION: n is a, t, c, or g

<400> SEQUENCE: 23
gtatccnnnn nn                                                       12

<210> SEQ ID NO 24
<211> LENGTH: 28
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (1)..(4)
<223> OTHER INFORMATION: n is a, t, g, or c

<400> SEQUENCE: 24
```
nnnntggtct tcgcttttgc gaagacca 28

<210> SEQ ID NO 25
<211> LENGTH: 34
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (1)..(8)
<223> OTHER INFORMATION: n is a, c, t, or g
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (32)..(34)
<223> OTHER INFORMATION: n is a, c, t, or g

<400> SEQUENCE: 25
nnnnnnnngg agaccgcttt tgcggtctcc nnnn 34

<210> SEQ ID NO 26
<211> LENGTH: 62
<212> TYPE: DNA
<213> ORGANISM: Artificial sequence
<220> FEATURE:
<223> OTHER INFORMATION: circular oligonucleotide
<220> FEATURE:
<221> NAME/KEY: misc_feature
<222> LOCATION: (1)..(4)
<223> OTHER INFORMATION: n is a, t, g, or c
<220> FEATURE:
<221> NAME/KEY: misc_feature
<222> LOCATION: (29)..(36)
<223> OTHER INFORMATION: n is a, t, g, or c
<220> FEATURE:
<221> NAME/KEY: misc_feature
<222> LOCATION: (59)..(62)
<223> OTHER INFORMATION: n is a, t, g, or c

<400> SEQUENCE: 26
nnnntggtct tcgcttttgc gaagaccann nnnnnnggag accgcttttg cggtctccnn 60 nn 62

<210> SEQ ID NO 27
<211> LENGTH: 36
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (1)..(9)
<223> OTHER INFORMATION: n is a, t, c, or g
<220> FEATURE:
<221> NAME/KEY: misc_feature
<222> LOCATION: (33)..(36)
<223> OTHER INFORMATION: n is a, t, c, or g

<400> SEQUENCE: 27
nnnnnnnntg gtcttcgctt ttgcgaagac cannn 36

<210> SEQ ID NO 28
<211> LENGTH: 26
<212> TYPE: DNA
<213> ORGANISM: Artificial sequence
<220> FEATURE:
<223> OTHER INFORMATION: oligonucleotide

```
<220> FEATURE:
<221> NAME/KEY: misc_feature
<222> LOCATION: (1)..(4)
<223> OTHER INFORMATION: n is a, t, c, or g

<400> SEQUENCE: 28
nnnnggagac cgcttttgcg gtctcc                                          26

<210> SEQ ID NO 29
<211> LENGTH: 78
<212> TYPE: DNA
<213> ORGANISM: Artificial sequence
<220> FEATURE:
<223> OTHER INFORMATION: circular oligonucleotide
<220> FEATURE:
<221> NAME/KEY: misc_feature
<222> LOCATION: (1)..(16)
<223> OTHER INFORMATION: n is a, t, c, or g
<220> FEATURE:
<221> NAME/KEY: misc_feature
<222> LOCATION: (41)..(56)
<223> OTHER INFORMATION: n is a, t, c, or g

<400> SEQUENCE: 29
nnnnnnnnnn nnnnnntggt cttcgctttt gcgaagacca nnnnnnnnnn nnnnnnggag     60
accgcttttg cggtctcc                                                   78

<210> SEQ ID NO 30
<211> LENGTH: 66
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (1)..(24)
<223> OTHER INFORMATION: n is a, t, c, or g
<220> FEATURE:
<221> NAME/KEY: misc_feature
<222> LOCATION: (47)..(66)
<223> OTHER INFORMATION: n is a, t, c, or g

<400> SEQUENCE: 30
nnnnnnnnnn nnnnnnnnnn nnnnggagac cgcttttgcg gtctccnnnn nnnnnnnnnn     60 nnnnnn                                                                66

<210> SEQ ID NO 31
<211> LENGTH: 68
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (1)..(24)
<223> OTHER INFORMATION: n is a, t, c, or g
<220> FEATURE:
<221> NAME/KEY: misc_feature
<222> LOCATION: (49)..(68)
<223> OTHER INFORMATION: n is a, t, c, or g

<400> SEQUENCE: 31
nnnnnnnnnn nnnnnnnnnn nnnntcctct tcgctttgc gaagaccann nnnnnnnn        60 nnnnnnnn                                                              68
```

METHOD FOR THE SYNTHESIS OF DNA FRAGMENTS

CROSS REFERENCE TO RELATED APPLICATIONS

This application is a continuation of U.S. application Ser. No. 10/009,926, file on Dec. 6, 2001, now abandoned, which is a 371 of PCT/DE00/01863 filed on Jun. 7, 2000 which claims priority under 35. U.S.C. Section 119(a) to German Patent Application 19925862.7 filed on Jun. 7, 1999, all of which are hereby incorporated by reference.

BACKGROUND OF THE INVENTION

According to the present state of the art about 50 different partially overlapping ca. 80 mer oligonucleotides have to be firstly synthesized and purified for the synthesis of an approximately 2.5 kb nucleic acid sequence. These are then hybridized in pairs or in subsets and filled in by means of a Klenow polymerase reaction or are constructed in a polymerase chain reaction (PCR) using the external oligonucleotides as primers and unidirectionally linked together (usually by means of restriction sites that have to be incorporated). This method is known as the gap filling method. Alternatively gene fragments can be synthesized by enzymatic or chemical ligation; these fragments can then be assembled to form larger gene sections after purification and/or cloning (so-called cassette method). Both procedures require at least one week in an ideal case but usually require closer to 6-12 weeks and even 6 months. Sequential processes bound to solid phases only have low yields due to the many reaction steps that are required and are therefore also very unreliable.

One of the main problems is that longer oligonucleotides always have an unavoidable portion of termination products due to the coupling efficiency which only reaches 99% per step even in syntheses which progress well. Furthermore deletions also occur which result from non-100% capping. Even in very good syntheses this portion is about 0.25% per coupling step. The separation of the trityl protective groups after completion of the synthesis also does not proceed completely. The incomplete oligonucleotide products that are formed in this manner cannot be completely separated from longer oligonucleotides even with much effort.

With an average coupling efficiency of 98%, one for example obtains a yield of the desired product of complete length of only 19.86% in the case of an 80 mer. With the currently available purification methods the desired end-product can at best be obtained in a purity of 95%. Even if only a small portion of the finally purified oligonucleotides is defective, the probability of a defective final sequence increases dramatically with the number of oligonucleotides that are used. Hence a sequence which is composed of 50 of the described oligonucleotides is only correct in 7.7% of all cases and therefore usually has to be re-worked. This does not take into account the relatively rare incorporation of false bases due to false coupling during the synthesis.

Due to the variety of potential sequences of even relatively short oligonucleotides (there are over $10^{18}$ possible sequence variants even of a 30 mer) it is also practically impossible to reuse oligonucleotides for various gene constructs. Hence it is technically not feasible to have available all the oligonucleotides required to generate any sequences. New oligonucleotides have to be synthesized and purified for each new gene construct. However, only a fraction of the synthesized material is actually used for the gene synthesis, the remainder cannot be utilized due to the reasons described above. The unsolved incorporation of oligonucleotide synthesis and purification in the process of gene synthesis is one of the main obstacles to a complete automation of this process which at present is technically extremely difficult and probably practically impossible to accomplish.

SUMMARY OF THE INVENTION

Hence the object of the present invention is to provide a method for the efficient synthesis of double-stranded DNA fragments of any sequence and length. A further object is to provide a method which allows any DNA molecule to be constructed from a limited library of basic building blocks. A further object is to demonstrate a method which allows the parallel synthesis and sequence-independent linkage of any gene fragments. Both these prerequisites have to be met in order to completely automate the gene synthesis process. A further object is to provide a kit for the automated production of double-stranded DNA fragments.

The object is achieved by providing a method for the production of a nucleic acid molecule comprising the steps:
a) Coupling one end of an oligonucleotide to a solid matrix wherein the coupling is effected by means of a modification and the oligonucleotide contains a recognition sequence for a type IIS restriction enzyme which cleaves outside its recognition sequence,
b) adding an additional oligonucleotide which is at least partially double-stranded
   and contains a different recognition sequence than in step a) for a type IIS restriction enzyme which cleaves outside its recognition sequence, whereby this oligonucleotide cannot bind to the matrix,
c) ligating the oligonucleotides from steps a) and b) in the orientation given by the blockage of the ends that are not to be ligated,
d) removing non-consumed reactants and enzymes,
e) cleaving the ligation product from step c) with a type IIS restriction enzyme which cleaves outside its recognition sequence whereby the cleavage occurs
in
   the oligonucleotide from step a),
f) separating the nucleic acid molecule obtained from the reaction mixture.

The object is additionally achieved by providing a method for producing a nucleic acid molecule comprising the steps:
a) to d) as above,
e) cleaving the ligation product from step c) with a type IIS restriction enzyme which cleaves outside its recognition sequence whereby the cleavage occurs
in
   the nucleic acid sequence of the oligonucleotide from step b),
f) separating the reaction mixture from the elongated oligonucleotide from step a) that is obtained in step e),
g) repeating steps b) to f) at least once.

The object is additionally achieved by providing a method for producing a nucleic acid molecule comprising the steps:
a) to g) as above,
h) cleaving the resulting nucleic acid molecule with a type IIS restriction enzyme which cleaves outside its recognition sequence whereby the cleavage occurs
in
   the oligonucleotide from step a) and optionally
i) cleaving the resulting nucleic acid molecule with a type IIS restriction enzyme which cleaves outside its recognition sequence whereby the cleavage occurs
in
   the oligonucleotide from step b).

A method is preferred in which an exonuclease and/or phosphatase reaction is carried out as step c)' after step c).

Furthermore a method is preferred in which the reaction mixture of step c)' is removed after the reaction. A method is additionally preferred in which step e) is not carried out in the last repetition of steps b) to f). A method is also preferred in which the resulting nucleic acid is separated from the oligonucleotide from step a) by restriction cleavage. Moreover a method is preferred in which the oligonucleotide from step a) is coupled to the solid matrix by means of a modification. A method is particularly preferred in which the modification is a biotin residue, a digoxigenin residue, a fluorescein isothiocyanate (FITC), an amino compound or a succinyl ester. Furthermore a method is preferred in which the oligonucleotide from step a) and/or b) has a loop. A method is particularly preferred in which the oligonucleotide from step a) is coupled by means of the loop to the solid matrix. A method is especially preferred in which the solid matrix is a bead, preferably made of glass or polystyrene, a microscope slide, a DNA chip, a well of a microtitre plate or a test tube. In particular a method is preferred in which the solid matrix comprises a streptavidin residue, an anti-digoxigenin antibody or an anti-FITC antibody. Furthermore a method is preferred in which the oligonucleotides from steps a) and b) have mutually complementary single-strand overhangs at their ends to be ligated. A method is especially preferred in which the single-strand overhangs are 1, 2, 3, 4 or 5 nucleotides long. A method is especially preferred in which the synthesized nucleic acid is linked in a final step to a replicable DNA (a plasmid vector, a phage or virus DNA, an artificial chromosome, a PCR product or another artificially produced DNA). A method is particularly preferred for producing codon-optimized open reading frames, for the directed mutagenesis of promoters, enhancers or DNAs which code for proteins. In particular the nucleic acid according to the invention is preferably used as a codon-optimized DNA vaccine, for the mutation analysis of protein domains, as a template for designer proteins, as an expression construct for in vitro protein synthesis, to prepare ribozymes or aptamers, as a probe for the detection of pathogenic microorganisms, as a probe for the detection of gene expression, for the detection of allele-specific mutations, for the detection of protein/protein binding, protein/peptide binding and/or binding of low-molecular substances to proteins.

The object is furthermore achieved by providing a kit for the production of a nucleic acid by the method according to the invention comprising:
a) a library of 1 to 1,048,576 different oligonucleotides wherein the oligonucleotides can be coupled to a solid matrix by means of a modification at one end and the oligonucleotide contains a recognition sequence or a part of the recognition sequence for a type IIS restriction enzyme which cleaves outside its recognition sequence,
b) an additional library of 4 to 1,048,576 different oligonucleotides wherein each of the oligonucleotides contains a recognition sequence for a type IIS restriction enzyme which cleaves outside its recognition sequence which is different from the type IIS restriction enzyme from a), and optionally contains the other part of the recognition sequence of the restriction enzyme from step a),
c) a solid matrix,
d) reservoirs for the enzymes required to produce the nucleic acid molecule and/or other reagents.

A kit is preferred in which the enzymes comprise a ligase or topoisomerase and/or one or several restriction enzyme(s) and/or an exonuclease and/or a phosphatase. An automated machine which can determine all reaction steps after the desired base sequence has been entered and automatically process them is particularly preferred.

BRIEF DESCRIPTION OF THE DRAWINGS

The invention is further elucidated by the following figures.

DETAILED DESCRIPTION OF THE INVENTION

Definitions

Figure 1:
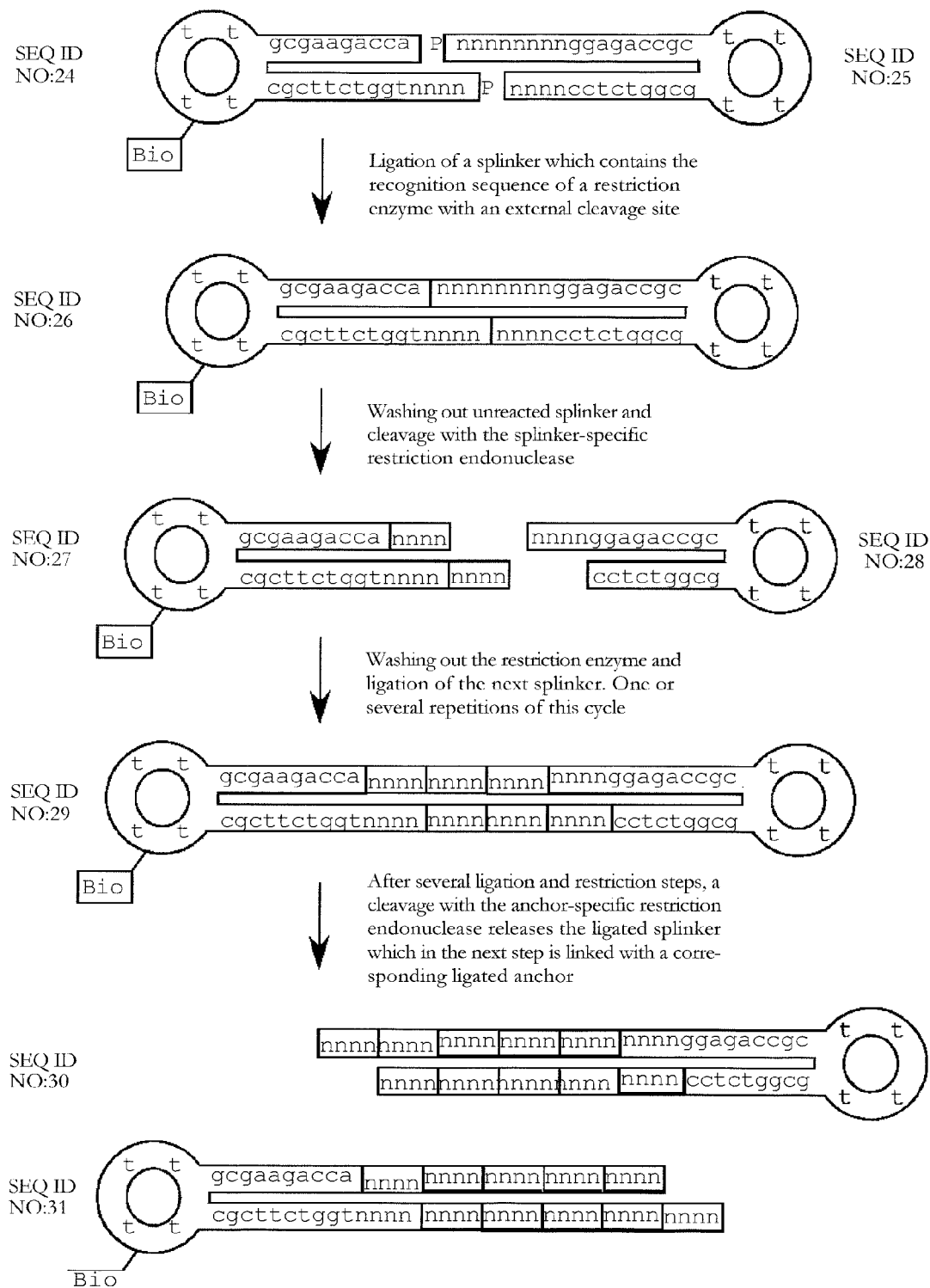
FIG. 1 shows a schematic representation of the method according to the invention. Bio means a modification (e.g. biotin) which is used to couple the anchor oligonucleotide to a solid matrix (e.g. streptavidin). For convenience, the polynucleotides are used in the drawing simply as an illustration of a method of the invention, and have been designated SEQ ID NOs:24-31. The illustrative sequences are not intended to limit the invention in any way. In this example, two polynucleotides of SEQ ID NOs:24 ("Anchor Oligo") and 25 ("Splinker Oligo") are ligated to form a single polynucleotide of SEQ ID NO:26; the anchor oligo is attached to a support via the modification ("Bio"), and the Splinker Oligo and the Anchor Oligo each harbor endonuclease cleavage sites that differ from each other. The ligated polynucleotide is cleaved using an endonuclease that cleaves at the cleavage site, and the unanchored polynucleotide (SEQ ID NO:28) is washed away; the anchored polynucleotide (SEQ ID NO:27) is retained, now containing the sequence of SEQ ID NO:24 with sequence fragments of SEQ ID NO:25, as illustrated. The cycle is repeated as desired with subsequent ligations of splinker polynucleotides and endonuclease cleavages, resulting ultimately in a polynucleotide that has been synthesized as desired, such as that represented by SEQ ID NO:29. The polynucleotide, thus grown, is then cleaved with an anchor-specific endonuclease to release the ligated splinker, creating two polynucleotides such as SEQ ID NOs:30 and 31. T, G, C, A and N denote the nucleic acid bases whereby T denotes thymidine, G guanidine, C cytosine, A adenine and N denotes any of the four nucleic acid bases.
Figure 2:
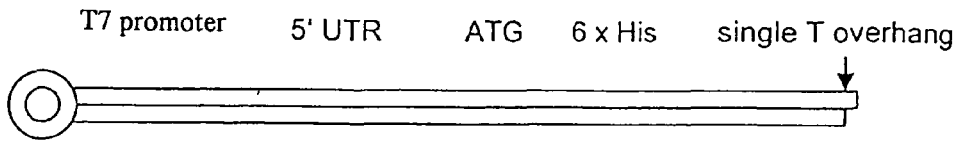
FIG. 2 shows schematically the structure of an EASYPRO™ transcription/translation system of PCR fragments. Bio denotes a modification which is used to couple the anchor oligonucleotide to a solid matrix. 5'-UTR denotes the 5' untranslated region. ATG denotes the start codon. 6×His denotes a sequence of six histidine codons. Single T overhang denotes an overhang of one thymidine residue.
Figure 3:
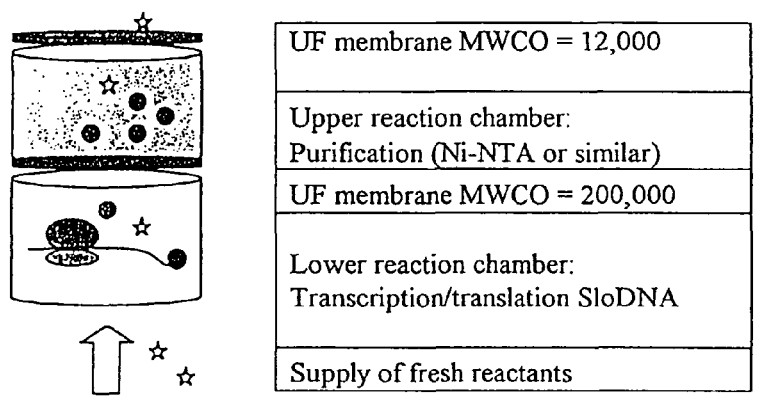
FIG. 3 shows a schematic representation of a minireactor for protein synthesis.
Figure 4:
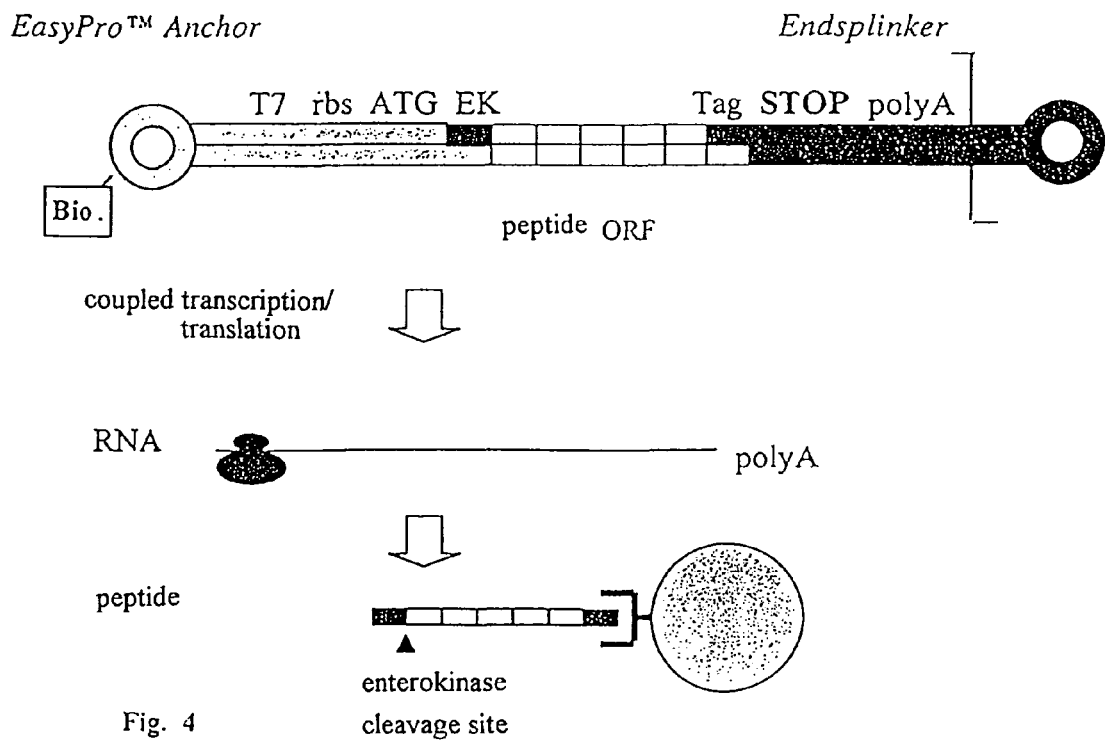
FIG. 4 shows a schematic representation of the production of a peptide library using the QUICKPEP™ method. Bio denotes a modification which is used to couple the anchor oligonucleotide to a solid matrix. T7 denotes the T7 promoter. rbs denotes an internal ribosomal binding site. ATG denotes the start codon. EK denotes an enterokinase cleavage site. Peptide ORF denotes the open reading frame of the peptide. STOP denotes the stop codon. Poly A denotes the poly A tail.
Figure 5:
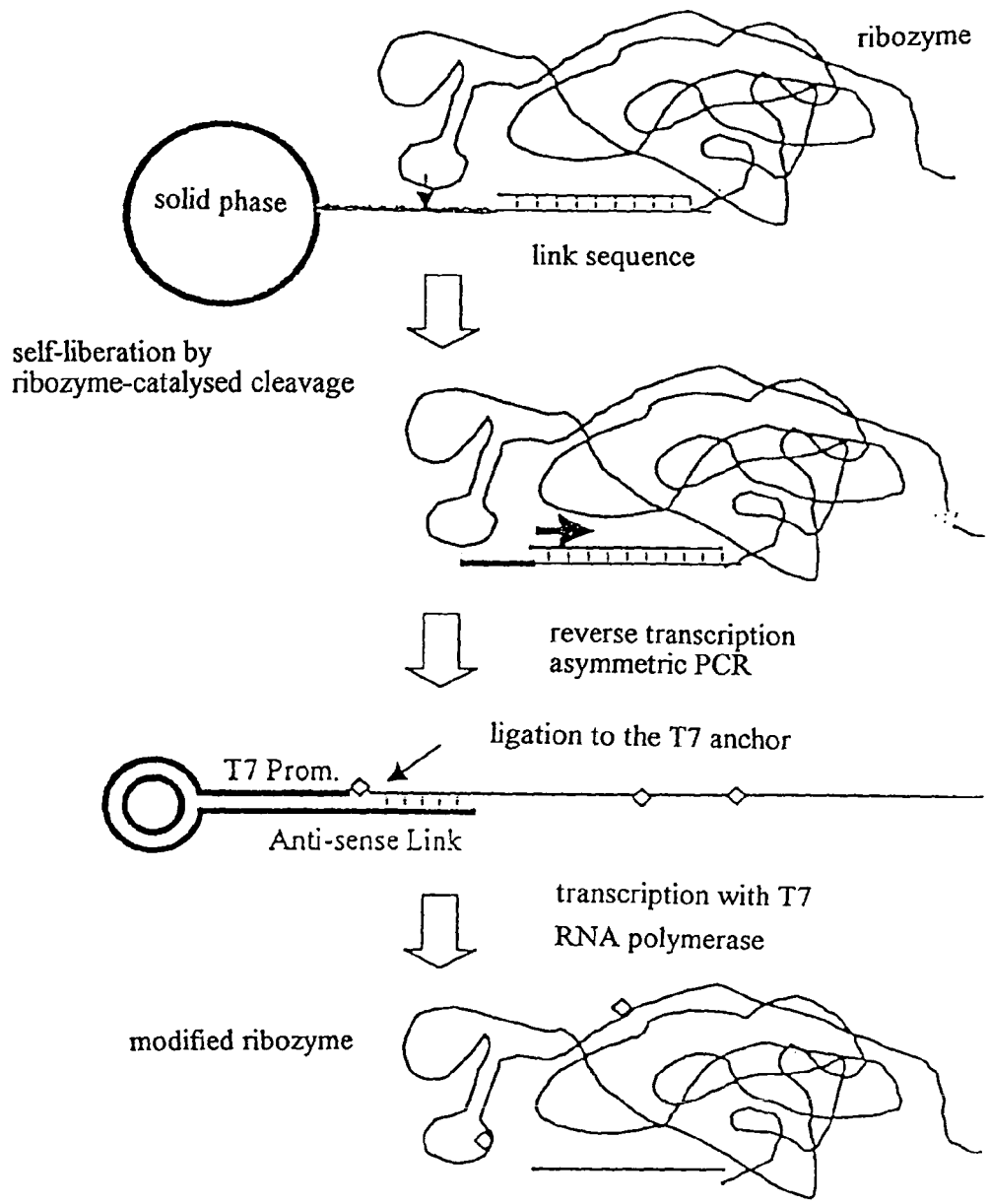
FIG. 5 shows a schematic representation of the selection of ribozymes using the RIBOSELECT™ method.
Figure 6:
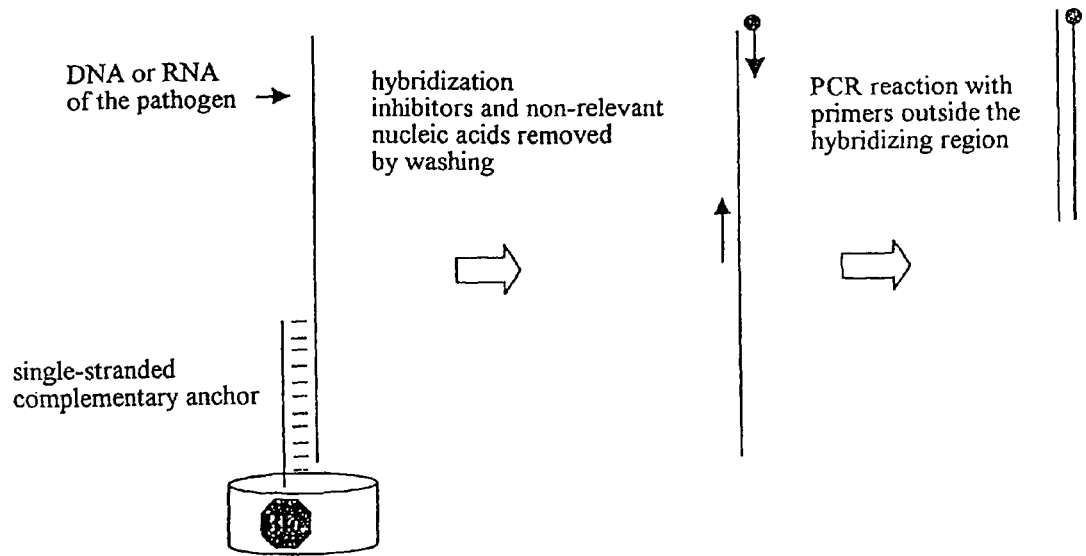
FIG. 6 shows a schematic representation of the detection of pathogens after amplification by PCR (PATHOCHECK™). Bio denotes a modification which is used to couple the anchor oligonucleotide to a solid matrix.
Figure 7:
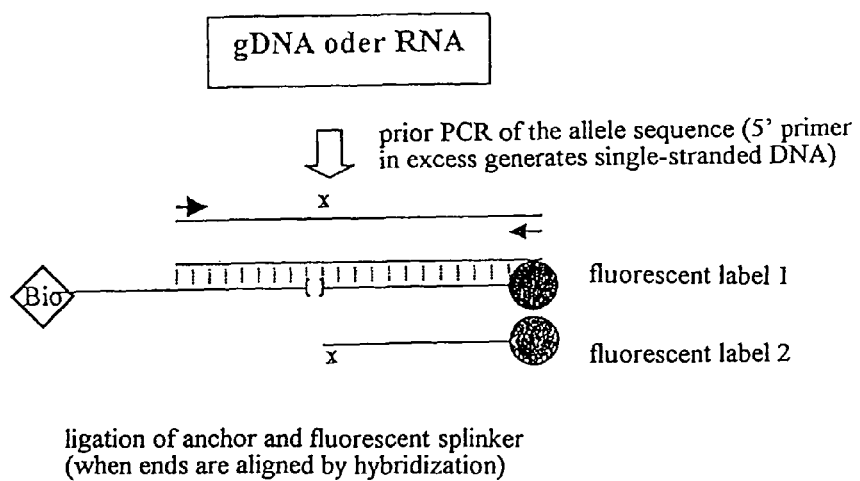
FIG. 7 shows a schematic representation of the identification of known alleles by ligating labelled splinkers (LIMA™). Bio denotes a modification which is used to couple the anchor oligonucleotide to a solid matrix. x denotes the site at which the modification to be determined is present.
Figure 8:
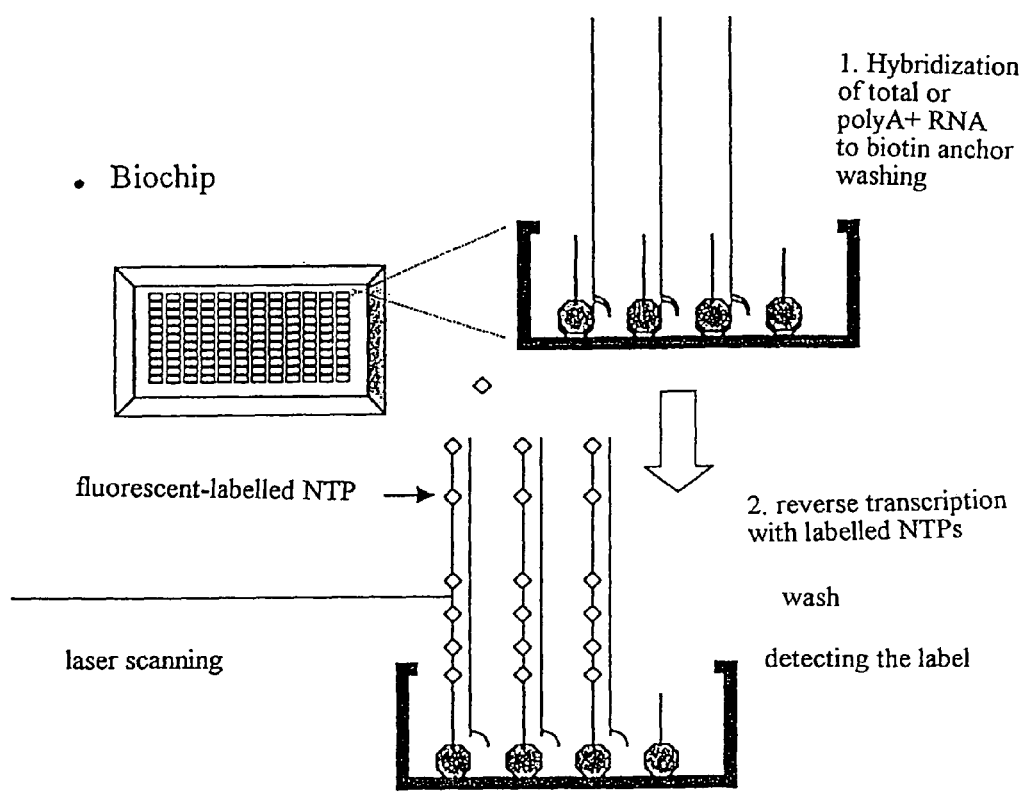
FIG. 8 shows a schematic representation of the parallel analysis of mRNA arrays (PAMINA™).

The term "parallel" or "parallel synthesis" as used herein means that different inventive nucleic acid molecules can be synthesized simultaneously in separate reaction mixtures in order to then be ligated e.g. as an anchor or splinker using the method according to the invention to form an elongated nucleic acid molecule.

The term "sloning" (sequential ligation of oligonucleotides in a sequence-independent manner) as used herein refers to a method for the successive ligation of oligonucleotides of any sequence.

The term "anchor" or "anchor oligonucleotide" as used herein refers to an oligonucleotide which can be coupled by means of a modification to a solid matrix. Within the scope of the present invention the oligonucleotide in its double-stranded region additionally contains a restriction cleavage site for a type IIS restriction enzyme which cleaves outside its recognition sequence.

The term "splinker" or "splinker oligonucleotide" as used herein refers to an oligonucleotide which has no modification or another type of modification and consequently does not itself bind to the matrix to which the anchor oligonucleotides are coupled.

The term "dumbbell" as used herein refers to a DNA structure which is characterized by a double strand that is flanked by two loops.

One aspect of the present invention concerns a method for producing a nucleic acid molecule comprising the steps:
a) Coupling one end of an oligonucleotide to a solid matrix wherein the coupling is effected by means of a modification and the oligonucleotide contains a recognition sequence for a type IIS restriction enzyme which cleaves outside its recognition sequence,
b) adding an additional oligonucleotide which is at least partially double-stranded
and contains a different recognition sequence than in step a) for a type IIS restriction enzyme which cleaves outside its recognition sequence, whereby this oligonucleotide cannot bind to the matrix,
d) ligating the oligonucleotides from steps a) and b) in the orientation given by the blockage of the ends that are not to be ligated,
h) removing non-consumed reactants and enzymes,
i) cleaving the ligation product from step c) with a type IIS restriction enzyme which cleaves outside its recognition sequence whereby the cleavage occurs
in
the oligonucleotide from step a),
j) separating the nucleic acid molecule obtained from the reaction mixture.

A further aspect of the invention concerns a method for producing a nucleic acid molecule comprising the steps:
a) to d) as above,
e) cleaving the ligation product from step c) with a type IIS restriction enzyme which cleaves outside its recognition sequence whereby the cleavage occurs
in
the nucleic acid sequence of the oligonucleotide from step b),
f) separating the reaction mixture from the elongated oligonucleotide from step a) that is obtained in step e),
g) repeating steps b) to f) at least once.

A further aspect of the invention concerns a method for producing a nucleic acid molecule comprising the steps:
a) to g) as above,
h) cleaving the resulting nucleic acid molecule with a type IIS restriction enzyme which cleaves outside its recognition sequence whereby the cleavage occurs
in
the oligonucleotide from step a) and optionally
i) cleaving the resulting nucleic acid molecule with a type IIS restriction enzyme which cleaves outside its recognition sequence whereby the cleavage occurs
in
the oligonucleotide from step b).

One of the two oligonucleotides that are to be linked in each reaction step (the so-called anchor oligonucleotide) can be coupled to a solid matrix by means of a modification e.g. a low-molecular chemical compound such as biotin or digoxigenin. In a preferred embodiment these are magnetic streptavidin-coated or anti-digoxigenin-coated beads. The other oligonucleotide (the so-called splinker oligonucleotide) also has a blocked end but does not have such a modification or has another type of modification. The important point is that the anchor oligonucleotides can be separated from the splinker oligonucleotides by binding to a suitable matrix. Hence any compounds e.g. biotin, digoxigenin, fluorescein isothiocyanate (FITC), amino compounds, succinyl esters and other compounds familiar to a person skilled in the art can be used provided they are suitable for mediating a direct or indirect (e.g. by means of an antibody) binding to a solid phase.

Anchor oligonucleotides can either be composed of a single, partially self-complementary oligonucleotide which can be coupled to a solid phase by means of a modification preferably in the loop sequence, or of two single-stranded oligonucleotides which form a double strand which preferably has a single strand overhang. Since only one of the two strands has to be coupled to a matrix, the other can be denatured and separated, if necessary, by alkali or heat (in order for example to serve as a template for a PCR reaction). In order to make sure that also in the case of such bipartite anchor oligonucleotides only one end can be ligated, the ends that are not required for the ligation are blocked accordingly. Nucleic acid sequences of typical anchor oligonucleotides are

Figure 9:
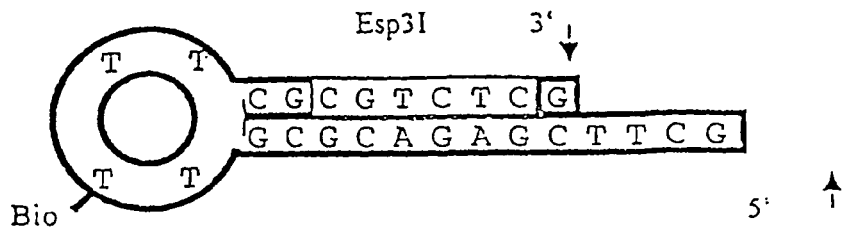
FIG. 9 shows the schematic representation of an anchor oligonucleotide, SEQ ID NO: 1. Bio denotes a modification which is used to couple the anchor oligonucleotide to a solid matrix. T, G, C, A denote nucleic acid bases whereby T denotes thymidine, G guanine, C cytosine, A adenine. Esp3I refers to a restriction enzyme.

```
                                    (SEQ ID NO: 1; FIG. 9)
anchor A3I  5'-GCTTCGAGACGCGTTTTCGCGTCTCG-3'

Figure 10:
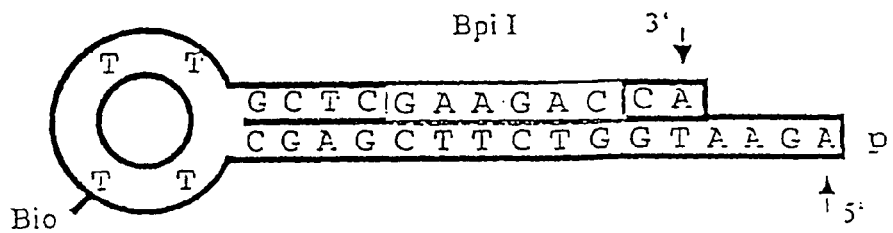
FIG. 10 shows the schematic representation of an anchor oligonucleotide, SEQ ID NO:2. Bio denotes a modification which is used to couple the anchor oligonucleotide to a solid matrix. T, G, C, A denote the nucleic acid bases whereby T denotes thymidine, G guanine, C cytosine, A adenine. BpiI refers to a restriction enzyme.

(SEQ ID NO: 2; FIG. 10)
anchor A2+  5'-AGAATGGTCTTCGAGCTTTTGCTCGAAGACCA-3'

Figure 11:
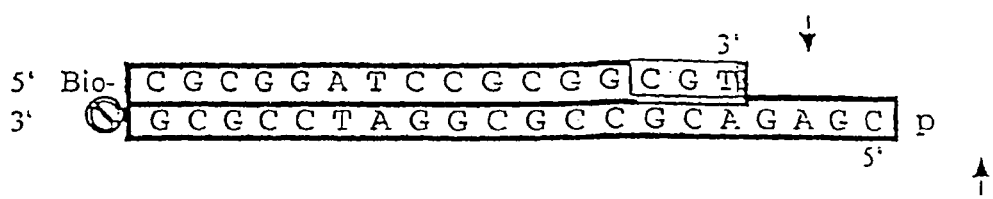
FIG. 11 shows the schematic representation of a bipartite anchor oligonucleotide. Bio denotes a modification which is used to couple the anchor oligonucleotide to a solid matrix. T, G, C, A denote the nucleic acid bases whereby T denotes thymidine, G guanine, C cytosine, A adenine. The top oligonucleotide with the "Bio" indication is SEQ ID NO:3, the bottom oligonucleotide is SEQ ID NO:4.
Figure 12:
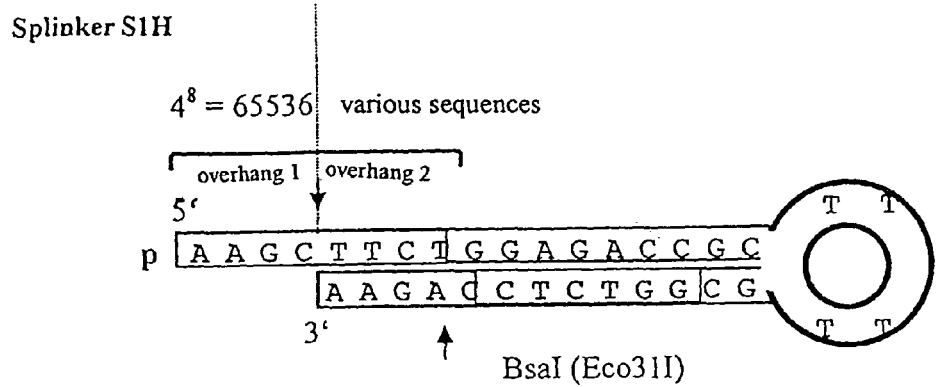
FIG. 12 shows the schematic representation of a splinker oligonucleotide, SEQ ID NO:5. T, G, C, A denote the nucleic acid bases whereby T denotes thymidine, G guanine, C cytosine, A adenine. BsaI and Eco31I refers to restriction enzymes.

(SEQ ID NO: 3; FIG. 11)
bipartite   5'-CGCGGATCCGCGGCGT-3
anchor (SEQ ID NO: 4; FIG. 12)
            5'-CGAGACGCCGCGGATCCGCG-3'
```

Splinker oligonucleotides can either be composed of a single, partially self-complementary oligonucleotide or of two single-stranded oligonucleotides which form a double strand preferably with a single strand overhang i.e. one has an at least partially complementary pair of oligonucleotides and the respective ends at the two single strands that are not to be ligated have to be blocked. The preferred single strand overhang sequence must be complementary to the respective anchor oligonucleotide that is to be ligated. Nucleic acid sequences of exemplary splinker oligonucleotides are

```
                                    (SEQ ID NO: 5, FIG. 12)
splinker S5H-AAGCTTCTGGAGACCGCTTTTGCGGTCTCCAGAA-3'

Figure 13:
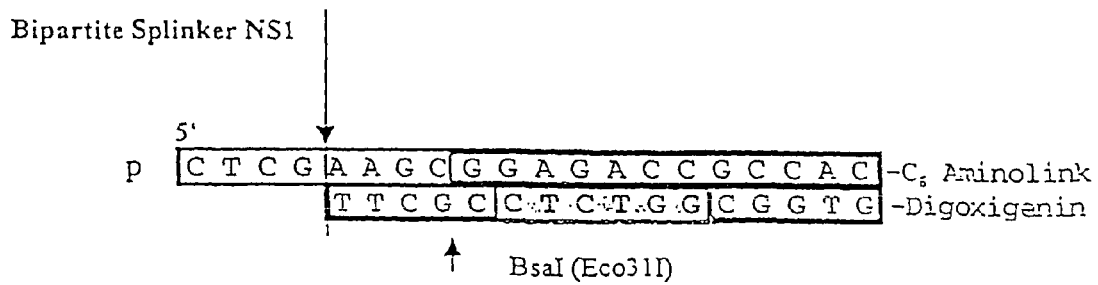
FIG. 13 shows the schematic representation of a bipartite splinker oligonucleotide. T, G, C, A denote the nucleic acid bases whereby T denotes thymidine, G guanine, C cytosine, A adenine. BsaI and Eco31I refers to restriction enzymes. The top oligonucleotide with the "BC$_6$ Aminolink" indication is SEQ ID NO:6, the bottom oligonucleotide is SEQ ID NO:7.
Figure 14:
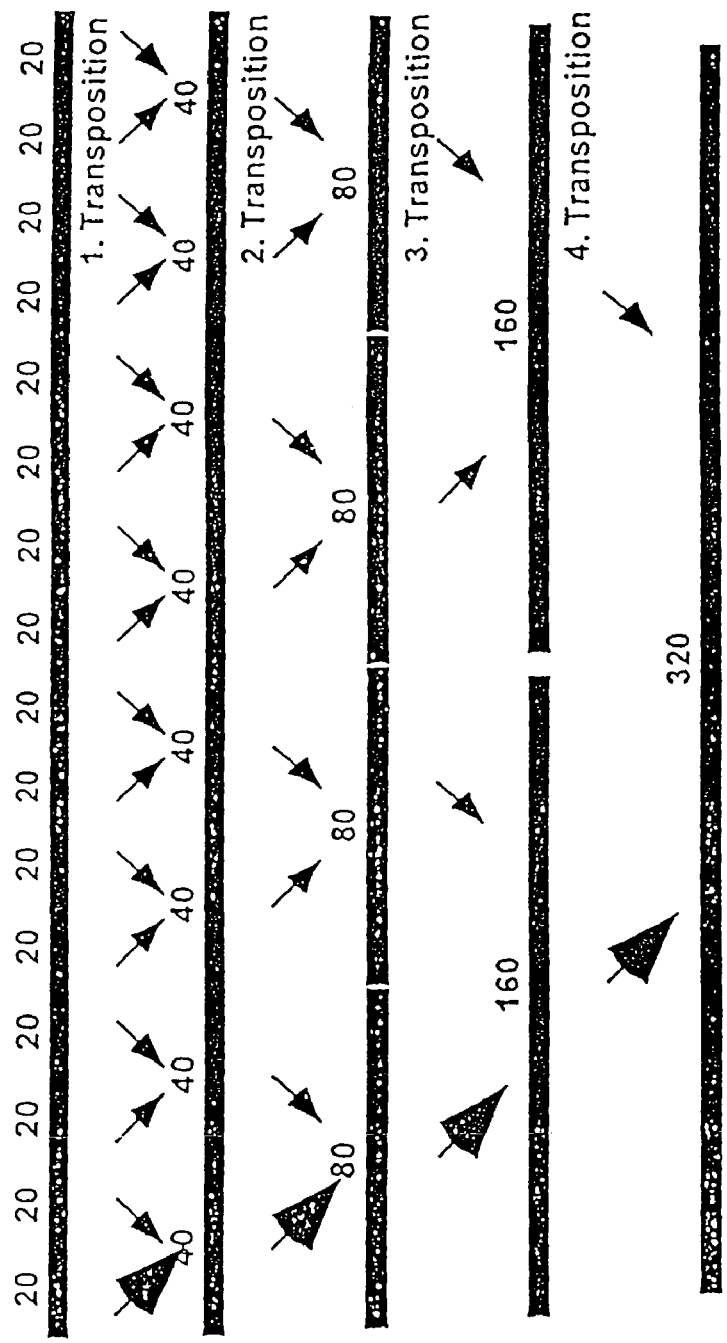
FIG. 14 shows a schematic representation of the synthetic pathway for long nucleic acids using the method according to the invention. The bars symbolize double-stranded DNA fragments which were synthesized in parallel by successive ligation/restriction cycles. Adjacent sections in the end product are in each case linked by ligating a ligated splinker with a ligated anchor. The large fragments obtained in this manner are then again cleaved in the next step either with the anchor-specific or with the splinker-specific restriction endonuclease and linked together by means of complementary overhangs etc. such that the length of the fragments doubles with each step. The linkage is completely independent of the sequence since the recognition sequences of the restriction endonucleases that are used are located in each case in the parts of the ligated fragments that are cleaved off and are therefore not incorporated into the growing nucleic acid. The numbers above the bars denote the size of the fragments in base pairs. Hence starting with DNA fragments of 20 base pairs in size this results in a maximum length of 320 base pairs after four transpositions, a length of 640 base pairs after five transpositions, a length of 1280 base pairs after six transpositions, a length of 2560 base pairs after seven transpositions etc.

(SEQ ID NO: 6; FIG. 13)
bipartite 5'-CTCGAAGCGGAGACCGCCAC-3'
splinker (SEQ ID NO: 7; FIG. 13)
          5'-GTGGCGGTCTCCGCTT-3'
```

Anchor as well as splinker oligonucleotides can contain overhangs of a defined length and, in a preferred embodiment, of one to five nucleotides. In the case of the oligonucleotides that are to be ligated these overhangs are complementary to one another, phosphorylated at the 5' end and can only be ligated together in one orientation. This results in a ligated oligonucleotide having for example a so-called dumbbell structure. In order to completely ligate all available anchor nucleotides, the splinker oligonucleotides to be ligated can be added in a two to ten-fold excess. The excess non-reacted splinkers are washed away with buffer after each ligation step. If, for example, streptavidin-coated magnetic beads are used, the beads containing the anchor oligonucleotides bound by means of a streptavidin/biotin bond together with the ligated splinkers can be retained in the reaction mixture by using a magnet. Alternatively it is for example possible to use wells, glass beads, microscope slides, DNA chips or any other solid phases which are directly coated with streptavidin. Beads are usually preferred because they have a larger surface and hence a higher binding capacity.

In order to carry out further ligations, a recognition sequence for a restriction endonuclease must be present which cleaves the nucleic acid sequence outside this recognition sequence in the ligated splinker oligonucleotide. Examples of such enzymes are BpiI, Esp3I, Eco31I, SapI etc. Restriction enzymes that are useful for the method according to the invention and their recognition sequences and cleavage sites may be found in the rebase data bank (Roberts, R. J., and D. Macelis (1999) REBASE—restriction enzymes and methylases. *Nucleic Acids Res* 27:312-3). The ligation products are cleaved at the restriction cleavage site contained in the splinker oligonucleotides in such a manner that a part of the splinker sequence remains on the anchor oligonucleotide. This also concurrently generates a sequence overhang which can be used to ligate an additional splinker oligonucleotide. The other cleaved part and the non-ligated remainder of the splinker oligonucleotide, the restriction enzyme and the restriction buffer are washed out of the reaction mixture whereupon a further cycle begins. The cycle can either be carried out only once or can be repeated several times before the oligonucleotides elongated in this manner are in turn linked to the concurrently synthesized neighbouring fragments. Since the mutually complementary overhangs formed by cleavage with the various restriction endonucleases are derived from the gene to be synthesized and, in contrast, the recognition sequences are located in the parts of the anchor or splinker oligonucleotides that have been cleaved off, the neighbouring fragments can be linked completely independently of their sequence. In particular this enables even large genes to be assembled in many concurrent partial reactions in only a few reaction steps. In the optimum case a 2 kb gene can for example be assembled in only 9 steps from 256 individual reactions. A gene of the same size would require more than 30 steps in the case of a linear synthesis (recursive, but not concurrent) and using 60 mer oligos. Since enzymatic as well as chemical ligation methods usually have yields of only 80-90%, the overall yield decreases exponentially with the number of required reaction steps which is why methods with few reaction steps are advantageous. In order to exclude non-reacted anchor oligonucleotides from the further synthesis, an exonuclease and/or phosphatase step can be optionally introduced after the ligation which removes the overhang or at least the 5' phosphate group required for the following ligation. The proportion of non-reacted anchor oligonucleotides is only small when an excess of splinker oligonucleotides is used. Moreover a subsequent reaction should only be possible when the same sequence is again ligated which is why the risk of contamination with non-reacted or only partially reacted anchor oligonucleotides can be regarded as relatively small.

The nucleic acid sequence that has been ligated on in this manner after several ligation and restriction cycles can subsequently be separated from the anchor oligonucleotide which remains on the matrix by cleavage with a restriction enzyme which specifically recognises a nucleic acid sequence in the original anchor oligonucleotide. The ligated nucleic acid sequence is now attached to the last ligated splinker oligonucleotide. After inactivation of the restriction enzyme, the elongated splinker oligonucleotide is transferred from the original reaction mixture into a new reaction vessel and linked there with a ligated anchor oligonucleotide which has been cleaved with a restriction enzyme that is specific for a splinker oligonucleotide (1st transposition). It is apparent to a person skilled in the art that the ligated nucleic acid sequences can be arbitrary sequences that can be different as well as identical. The ligation product resulting from the 1$^{st}$ transposition is in turn cleaved with an anchor-specific restriction endonuclease and again ligated with a ligated anchor oligonucleotide that has been obtained in a similar manner (2$^{nd}$ transposition). As a result the length of the ligated nucleic acid sequences then doubles with each additional step. The DNA fragments are in each case linked by means of complementary overhangs but this is otherwise completely sequence independent. The only constraint is that the anchor- and splinker-specific cleavage sites must not be present in the sequence to be synthesized because otherwise the DNA would also be cleaved internally. An exonuclease step can be optionally introduced in each case before cleavage at an anchor-specific restriction cleavage site and the subsequent transposition in order to prevent the transposition of incompletely ligated splinker oligonucleotides. The sequence-specific cleavages that are necessary for the method can in principle also be carried out by ribozymes with an analogous function instead of type IIS restriction endonucleases.

A double-stranded DNA sequence of 2560 base pairs in length can be synthesized from a 20 base pair sequence (which in the case of splinkers with a 4 nt overhang can be obtained by 5 successive ligations of the required original splinker from the library) by only 7 additional ligation steps. With cycle times of ca. 1 hour, an arbitrary DNA sequence of this length can be synthesized within 12 hours. The time required can be halved to about 6 hours by optimizing the reaction conditions.

In the case of overhangs of 4 nucleotides in length, a library of 65536 different splinker oligonucleotides is required to produce all possible nucleic acid sequences. This number results from the following calculation: there are 256 possible 4 nucleotide overhangs ($4^4$=256), there are an equal number of sequence variants for the four directly adjoining nucleotides which form the overhang in the next ligation step. Overall this results in a total number of $4^4$ times $4^4$=$4^8$=65536 splinker oligonucleotides which can be used to represent all possible sequence variants. In the case of 3 nucleotide overhangs the complexity of the required splinker library is reduced correspondingly to $4^3$ times $4^3$=4096, in the case of 2 nucleotide overhangs to $4^2$ times $4^2$=256 and in the case of 5 nucleotide overhangs it would increase to $4^5$ times $4^5$=1048576. A prerequisite for this building block system is the presence of a complete splinker library (for 2 nt overhangs 256 oligonucleotides, for 3 nt overhangs 4096 oligonucleotides, for 4 nt overhangs 65536 oligonucleotides and for 5 nt overhangs 1048576 oligonucleotides) and an anchor library (4, 16, 64, 256 or 1024 oligonucleotides with 1, 2, 3, 4 or 5 nt overhangs). However, the latter is not absolutely necessary since the various overhang sequences can be generated equally well by a prior ligation step using suitable splinker oligonucleotides.

In principle all individual steps of the method according to the invention can be automated and hence the production of complete genes is as simple as the synthesis of oligonucleotides. Moreover, the method according to the invention has a potential to considerably reduce the costs. Firstly all required enzymes can be produced on a large scale. Secondly the investment for the splinker library can be considerably reduced by synthesizing the individual splinker oligonucleotides en bloc with the exception of the last 4 nucleotides of the 5' overhang. The synthesis reaction is then divided into four equal portions; the four different nucleotides are then attached in separate reactions to the next (in the final product the fourth to last) position. Afterwards the four individual reactions are again quartered after which the third to last nucleotide is attached etc. Instead of 65536 individual syntheses one would then only require 256 syntheses on a correspondingly larger and hence more favourable scale. Furthermore the 256 possible 4 nucleotide overhangs can be generated by a blunt end ligation on 256 different anchor oligonucleotides, subsequent exonuclease treatment, washing and finally the restriction with the anchor-specific restriction endonuclease. In this manner the 65536 required splinker oligonucleotides could be prepared in a cost-effective manner. Moreover this would avoid a complicated purification of all 65536 splinker oligonucleotides since non-reactive faulty sequences are removed by this procedure. Since an extremely high purity of the used oligonucleotides is essential for successful faultless syntheses, these have to be in any case appropriately pretreated. In addition it is necessary to ensure that exonucleases are almost completely absent during the restriction and ligation steps so that the overhang sequences that are required for the subsequent ligations remain intact. These exonucleases must be thoroughly washed away and/or inactivated especially when intermediate exonuclease steps are used to remove non-ligated anchor oligonucleotides.

The anchor and splinker oligonucleotides can be each composed of a self-complementary single strand as well as of two complementary plus and minus strands. The nucleic acid sequences do not have to be completely complementary; the self-complementary single-strand oligonucleotides can have a loop and the complementary plus and minus strands can be partially complementary. In the case of anchor and splinker oligonucleotides that are each composed of two complementary plus and minus strands (i) the melting temperature of the double-stranded hybrid must be high enough to prevent denaturation of the assembled anchor and splinker oligonucleotides and a possible consequent unintentional transfer of the single strands that are not coupled to a solid phase and (ii) the respective ends that are not to be elongated have to be blocked by suitable modifications. Oligonucleotides consisting of two complementary plus and minus strands have certain advantages over oligonucleotides composed of a self-complementary single strand. Self-complementary (snap back) oligonucleotides often cause certain problems during the purification since at high concentrations they have a tendency to form networks. Single-stranded partial oligonucleotides are also shorter and can therefore be isolated with less effort in higher purity. Bipartite anchor oligonucleotides composed of two partial oligonucleotides are used for certain inventive embodiments.

In a specially preferred embodiment the anchors and splinkers contain the following combinations of recognitions sequences (SEQ ID NOs:8-23):

| anchor | splinker |
|---|---|
| CGTCTCN^NNNN_ (Esp3I, BsmBI) (SEQ ID NO: 8) | GGTCTCN^NNNN_ (BsaI, Eco31I, . . . ) (SEQ ID NO: 9) |
| GGTCTCN^NNNN_ (BsaI, Eco31I, . . . ) (SEQ ID NO: 10) | CGTCTCN^NNNN_ (Esp3I, BsmBI) (SEQ ID NO: 11) |

-continued

| anchor | splinker |
|---|---|
| GAAGACNN^NNNN_ (BbsI, BpiI . . . ) (SEQ ID NO: 12) | ACCTGCNNNN^NNNN_ (BspMI, Acc36I) (SEQ ID NO: 13) |
| ACCTGCNNNN^NNNN_ (BspMI, Acc36I) (SEQ ID NO: 14) | GAAGACNN^NNNN_ (BbsI, BpiI . . . ) (SEQ ID NO: 15) |
| GCAGTG_NN^ (BtsI) (SEQ ID NO: 16) | GCAATG_NN^ (BsrDI, Bse3DI, . . . ) (SEQ ID NO: 17) |
| GCAATG_NN^ (BsrDI, Bse3DI, . . . ) (SEQ ID NO: 18) | GCAGTG_NN^ (BtsI) (SEQ ID NO: 19) |
| GTATCCNNNNN_N^ (BciVI, BfuI) (SEQ ID NO: 20) | ACTGGGNNNN_N^ (BfiI, BmrI) (SEQ ID NO: 21) |
| ACTGGGNNNN_N^ (BfiI, BmrI) (SEQ ID NO: 22) | GTATCCNNNNN_N^ (BciVI, BfuI) (SEQ ID NO: 23) |

A further aspect of the present invention is a kit for the production of a nucleic acid by the method according to the invention. The kit can consist of a library of all necessary anchor and splinker oligonucleotides, in addition a solid phase to which the anchor oligonucleotides can be coupled, preferably magnetized beads, suitable reaction vessels, ligase, optionally a topoisomerase and/or a 3'-5' exonuclease and/or phosphatase, at least two different type II restriction endonucleases which cleave outside their recognition sequence and all required reaction buffers. In addition a pipetting station with a refrigerated sample storage container and an appropriate software control which automatically carries out all steps of the method according to the invention is preferred.

The present invention allows a complete automation of the entire process of gene synthesis by providing a library of reusable, at least partially double-stranded oligonucleotides in high purity containing recognitions sequences for certain type IIS restriction endonucleases (so-called outside cutters). Furthermore automation is made possible by the provision of a method which allows the parallel synthesis of gene fragments and their sequence-independent linkage at any desired site and by the oriented elongation of the starting molecules as a result of their binding to a solid phase (the ends that are not to be ligated are blocked by suitable modifications or loop sequences) and by a defined set of recursive procedures (ligation, washing and restriction steps) which can be processed by a robot.

Certain aspects of the present invention are illustrated by way of example in the following and are based on the complete synthesis of entire genes by the method according to the invention.

1. Production of a cDNA when Only the Protein Sequence is Known

If often occurs that only the amino acid sequence or parts of the amino acid sequence of a protein are known but not the cDNA or genomic sequence. Due to the degeneracy of the genetic code it is usually not possible to directly amplify the corresponding gene by a PCR of a suitable cDNA library. Hence one looks for regions in which there is an abundance of amino acids such as tryptophan, methionine or asparagine, aspartate, glutamate, glutamine, tyrosine, phenylalanine, cysteine or lysine since there are only one or two codons for these amino acids. If it is possible to obtain a PCR fragment of the expected size using primers of low degeneracy, this fragment is used as a probe in order to clone the respective gene from a cDNA bank. Although this work is nowadays considerably simplified in many cases by the availability of gene arrays and clone collections, such aids are only available for a limited number of organisms and cell types and, even if the complete cDNA is available, it is usually still necessary to redone it in a suitable expression vector. Depending on the difficulty of the project the time required can be one to two weeks and in extreme cases even several months to years. The method according to the invention can be used to prepare an expression construct having an optimized codon usage for the desired organism in one to two days starting from a known protein sequence. The organism in which the protein is naturally expressed does not have to be available at all for this since the DNA sequence can be derived from the known protein sequence without a template having to be available. As the protein sequencing methods improve, it will be possible in future to sequence proteins having interesting enzyme activities from any desired organisms and to transfer them directly by the method according to the invention into any desired expression system without having to take the indirect route via cDNA cloning.

2. Production of Designer Genes and Designer Proteins

A further aspect of the present invention is the simple production of designer genes and designer proteins i.e. the coupling of functional domains of various proteins in order to, for example, prepare enzymes having new or modified properties. If the X-ray crystal structure of a protein is known, it is then possible to make very specific modifications such as the insertion of defined linker domains or a redesign of a binding pocket in order to introduce new functions of modified specificities into proteins. For example targeted protein design can be used to construct regulatable catalytic centres which are activated by a change in the conformation of the protein as a result of the binding of a specific ligand. Designer proteins can be constructed in this manner which for example develop a caspase activity when a particular virus protein binds which then triggers apoptosis in the infected cells. First versions of such highly specific pharmaceutical agents have already been described; cf. Vocero-Akbani A. M., Heyden N. V., Lissy N. A., Ratner L., Dowdy S. F., Nat. Med. 1999 Jan, 5:1, 29-33. Furthermore proteins can be stabilized by incorporating amino acids that can form additional salt bridges at particular positions. This can improve the tolerance towards high temperatures which, among others, is advantageous for the detergent industry. If the domain structures are known, a desired enzymatic activity can be separated from an undesired activity by the precise expression of certain functional regions. In addition it is also possible to construct multienzyme complexes which can catalyse a complete series of different reactions. This can improve the synthesis of many organic compounds or even enable some syntheses for the first time. This opens up completely new perspectives since many organic syntheses in which environmentally hazardous solvents and catalysts still have to be currently used can be replaced in the future by such designer biocatalysts.

3. Systematic Mutagenesis as a Substitute for Randomized Mutagenesis

A problem that often occurs in biochemically oriented molecular biology is to identify which of many protein variants have the highest enzymatic activity or the strongest binding to a substrate or another protein. The usual procedure is to introduce a series of random mutations of one or several amino acids and to analyse the resulting variants in a suitable screening process. Although in principle it is also possible to separately prepare all mutants, this is seldom carried out for reasons of time and costs. The control over the mutants that are formed in a randomized mutagenesis is by nature very limited since the process results in certain amino acid substitutions being found more frequently than others and also since it is hardly possible to avoid the additional introduction of stop codons in this procedure. In contrast the method according to the invention allows all desired mutants to be prepared in a specific manner and without too much effort and to be expressed as proteins.

4. Production of Synthetic Genes Especially for Use as DNA Vaccines

In many cases it is desirable to optimize the protein expression of certain genes in heterologous systems. Very often this can only be partially achieved by the use of strong promoters. Depending on which organism is used for the expression, the use of certain codons for an amino acid can have advantageous or disadvantageous effects on the achievable gene expression. Thus, for example, many retroviral gene products can only be poorly translated in eukaryotic cells since they are usually very AT rich and utilize rare codons in higher eukaryotes. Hence it is a major advantage, especially for an application of such gene sequences as DNA vaccines, when their codon usage is optimized for mammalian cells. Likewise certain RNA structures can lead to an instability of the transcripts which can also adversely affect the gene expression. Such elements can also easily be eliminated with the method according to the invention by codon changes.

5. Analysis of Protein Domains by Deletion or Point Mutagenesis

The analysis of mutants is very often the preferred method for the functional characterization of proteins. Although there are a number of established methods for producing deletion and point mutants, these are usually very time consuming and laborious. Deletions are usually produced by introducing linker sequences or by a PCR using primers whose ends are complementary to various partial sequences. In order to obtain an entire series of defined deletions, it is frequently necessary to carry out a two-step procedure in which firstly particular restriction cleavage sites are introduced which can then be used to introduce the desired deletions. Using appropriately designed primers and a multi-fragment ligation it is also in principle possible to carry out such deletions in one step but the chances of success are rather small. In all these cases the wildtype DNA has to be present as a template which is not necessary in the method according to the invention. Moreover deletion mutants can be produced since it is not necessary at all to introduce restriction cleavage sites for which one must firstly find suitable sites so that the introduced mutations do not result in changes in the protein sequence (so-called silent site mutations). The method according to the invention also allows the production of double or triplet mutants. For the functional mapping of a protein the above-mentioned silent site mutations can also be used to introduce restriction cleavage sites in its gene sequence for a large number of different restriction endonucleases with the aid of which any desired deletions can be produced. Hence in many cases the classical mutation analysis can be omitted and can be replaced by the more rapid and accurate method according to the invention.

6. Coupled In Vitro Transcription/Translation Systems ("EASYPRO"™)

Coupled in vitro transcription/translation systems are used to rapidly synthesize proteins on an analytical scale e.g. for binding studies or co-precipitation assays. For this the sequences to be expressed are cloned into a vector which contains a promoter for an RNA polymerase. This polymerase is used to transcribe mRNA which is translated in an RNA-depleted wheat-germ or reticulocyte extract into the desired protein that is usually radioactively labelled with $^{35}$S-methionine or cysteine because of the low yield and the simpler detectability. An even more rapid alternative is the EASYPRO™ system based on the method according to the invention. A single thymidine overhang that can be directly ligated with a PCR product is generated by restriction with XcmI in an anchor oligonucleotide which contains a T7 (SP6) promoter, an internal ribosomal binding site and a hexahistidine tag. Three EASYPRO™ anchor oligonucleotides having various reading frames are sufficient to translate all PCR fragments that are ligated in the correct orientation. Moreover terminal transferase or ligation of an appropriate splinker oligonucleotide to the 3' end of the PCR product can be used to easily introduce an artificial poly-A tail into the DNA template which stabilizes the RNA transcript and hence ensures a higher translation efficiency. Furthermore the DNA sequences coding for the desired protein can, after cleavage with a restriction endonuclease, also be directly ligated to a modified EASYPRO™ anchor having a matching 4 nt overhang.

A further aspect of the present invention is the provision of a minireactor for the rapid synthesis of proteins. The transcription of the expression-anchor nucleic acid sequence coupled to streptavidin-coated beads takes place in the lower reaction chamber of the minireactor. The resulting mRNAs are bound via their 3' poly-A tail to oligo-dT coupled beads which are also present in the lower reaction chamber. This is also where the mRNAs are translated in a reticulocyte extract. This chamber is separated by an ultrafiltration membrane having an MWCO (molecular weight exclusion) of ca. 200 kD from a second chamber which is located above. This chamber contains beads that can bind the protein of interest (e.g. $Ni^{2+}$-NTA beads for proteins with a hexahistidine tag). The production is maintained over a long period by a continuous supply of buffer solution containing fresh low-molecular reactants (amino-acyl-tRNAs, ribonucleotide triphosphates, CAP-analogue and creatinine phosphate). As a result the synthesized protein is at the same time pressed from the lower into the upper reaction chamber where it is captured on the beads. This chamber can be alternatively closed by an additional ultrafiltration membrane whose exclusion size is selected such that it is permeable to buffers and smaller molecules but not to the desired protein. Hence the protein collects in the upper chamber and can be isolated therefrom in a purified form. The achievable yields are not only adequate for most analytical experiments but can even replace protein expression experiments on a small scale. If it is for example intended to determine the specific enzymatic activity of various protein mutants, these had to be hitherto cloned, expressed and purified in complicated preliminary experiments. Since almost all these steps are already integrated in the EASYPRO™ method according to the invention this achieves a considerable time advantage over conventional methods.

A modification of the aforementioned method according to the invention can be used to simply and cheaply prepare peptide libraries which, among others, are required for the epitope mapping of antibodies or to identify immunogenic epitopes in proteins of viruses, bacteria or fungi (in order to rapidly set up serological detection systems). For this modified EASYPRO™ anchor oligonucleotides are successively elongated by splinker ligations to form sequences coding for the desired peptides. In the last step a preformed end splinker is ligated on which codes for a C-terminal tag, a stop codon and a poly-A tail. The ligation products are transcribed and translated in the described minireactor. After completion of the translation and several wash steps, the finished peptides are cleaved at the cleavage site coded by the EASYPRO™ anchor oligonucleotide using a specific protease, e.g. enterokinase or factor Xa, and washed out of the upper reaction chamber. These peptides can be bound with the aid of the C-terminal tag to a solid phase for subsequent tests. Moreover the peptides are already present in a purified form and can be directly used for subsequent applications. Since the same anchor oligonucleotide is used in each case and the required splinker oligonucleotides can be ligated on in a few steps from an already prefabricated section, the costs are less than with a conventional peptide synthesis.

7. Production Of Ribozymes Or Aptamers

In a similar manner to the protein synthesis described above the anchor oligonucleotide can also be used for the production and mutagenesis of RNAs using a T7 (SP6) promoter. The system is particularly suitable for the synthesis of various ribozymes since the DNA sequences coding for the ribozymes on an elongated splinker oligonucleotide can be ligated to a promoter module on an anchor oligonucleotide. Above all it is possible to prepare exactly defined ribozyme template libraries that can be readily amplified by PCR. Ribozyme template sequences can be accurately synthesized on the nucleotide using the method according to the invention without having to carry out cloning operations for this. Ribozymes can be prepared by introducing link sequences and these ribozymes can then be coupled to any chemical compound such as peptides, nucleic acids, aliphatic hydrocarbons, esters, ethers or alcohols by means of a DNA/RNA that is complementary to the link sequence. If this compound is present bound to a solid phase, ribozymes can be selected which cleave this bond. Those ribozymes which have "freed" themselves from the binding to the solid phase can be converted by reverse transcription and subsequent asymmetric PCR into single-stranded DNA molecules. These are then hybridized and ligated by the link sequence to an appropriately modified anchor oligonucleotide. The anchor oligonucleotide is constructed such that it contains a T7 promoter by means of which the ribozyme can be obtained again with the aid of a T7 polymerase. The use of an inaccurate reverse transcriptase (e.g. HIV RT) allows the introduction of random mutations. The selection pressure can be increased by increasingly shorter incubations such that ribozymes having a high activity are preferentially amplified. Ribozymes having the ability to mediate binding to the solid phase can be selected similarly using the same principle.

8. Use of ssDNAs Produced According to the Invention in Diagnostics (PATHOCHECK™)

The diagnosis of infectious diseases often requires a direct test for the pathogen e.g. by PCR. Especially in transfusion medicine it is important to be able to reliably detect and eliminate contaminated blood samples. The serological assays that are usually used can only guaranteed this when the donor has already been infected for some time so that antibodies have already been formed. For example in the case of a HIV infection no antibodies are detectable in the blood during a period of up to 12 weeks (and even longer in extreme cases) although a massive virus replication has already taken place. Since a routine PCR examination of all samples is hardly feasible in many places for cost reasons, this is carried out (if at all) on pools of individual donations. The problem with this is that it reduces the sensitivity which is otherwise very high since there is a limit to the amount of material that can be used for the analysis. In the case of viral diseases such as HIV in which the majority of the viruses are present extracellularly, this can be compensated fairly well by concentrating the viruses by centrifugation, but this is usually less effective in the case of viruses that are mainly associated with the cells. Although one can firstly isolate DNA or RNA from the blood cells, only a fraction thereof can be used in the PCR reaction since otherwise unspecific PCR products increase uncontrollably. Hence in such cases a preselection of the amplified material has to be carried out. A single-stranded product is used for this which has been produced by the method according to the invention using a modified anchor oligonucleotide. In this case an anchor oligonucleotide is used which is composed of two separate complementary strands one of which is modified at the 5' end e.g. biotinylated and the other is blocked at the 3' end. After synthesis of the viral sequence, the non-biotinylated strand is separated by washing with a denaturing solution such that a single-stranded antisense DNA remains. This can be amplified with the 5'-biotinylated partial anchor oligonucleotide and a terminal oligonucleotide if more material is required. Only one strand of this PCR product is biotinylated, the other can be separated by denaturation. This antisense DNA can now be used to enrich viral RNAs or DNAs from a complex mixture such as a cell lysate or a nucleic acid preparation by hybridizing them with one another, binding the hybrids to a streptavidin-coated support and washing away non-hybridized components under stringent conditions. In a second step the concentrated RNAs or DNAs can then be amplified by a conventional PCR using primers from the non-hybridized part of the RNA or DNA and detected. This is usually carried out by gel electrophoresis of the products or by fluorescence analysis or by a subsequent ELISA provided that an appropriately modified primer has been used. The advantages of the method according to the invention are that it is possible to use almost any amounts of starting material which improves the sensitivity of the analysis, it is also possible to examine several targets simultaneously and also to differentiate by using primers with different kinds of fluorescent labels, and that it can be used for any pathogens such as bacteria, fungi or viruses. The preconcentration of the sequences to be amplified also considerably reduces background problems. With an appropriate miniaturization it is possible to simultaneously test for a large number of different pathogens on one chip which considerably reduces the analytical costs.

9. Gene Profiling (GPRO™)

In molecular-biological research and increasingly also in molecular diagnostics the expression of certain genes is examined quantitatively at the RNA level. Standard tools for this are Northern Blot, 51 mapping or the ribonuclease protection assay (RPA) usually in conjunction with radioactively labelled probes. The single-stranded DNAs described above can also be used for this purpose. A prior purification of the RNAs to be analysed which usually represents an additional source of error is not necessary for this. Similarly to the PATHOCHECK™ method according to the invention, the mRNAs to be examined are hybridized with an excess of a modified, e.g. biotinylated, anchor oligonucleotide with gene-specific single-stranded antisense DNAs and immobilized for example on a streptavidin-coated solid phase. After washing out all proteins, non-relevant nucleic acids and other impurities, the target mRNAs are detected with a series of direct or indirect fluorescent labelled splinker sequences which are complementary to another part of these mRNAs. The use of different gene-specific antisense DNAs and differently labelled detection splinker oligonucleotide enables the simultaneous analysis of the expression of several genes. The entire method can be completely automated in an uncomplicated manner. If the tissue to be analysed does not contain a large amount of RNase, a lysis in chaotropic buffers and/or the addition of RNasin is sufficient to ensure the integrity of the RNAs. If a maximum sensitivity is more important than the simultaneous detection of different mRNAs in a reaction mixture, antibodies which bind to a polyvalent secondary reagent such as an anti-mouse Ig-peroxidase polymer can be used instead of the fluorescence-based detection reagents. These complexes are then detected in a subsequent enzymatic reaction e.g. by means of the chemiluminescence generated by reaction of a suitable substrate. In the case of investigations that are carried out particularly frequently, GPRO™ kits containing synthetic control mRNAs as quantitative standards can be formulated in advance.

10. Allele Identification by Hybrid-Mediated Ligation (LIMA™; Ligation Mediated Identification of Mutant Alleles)

The genotype of certain alleles has to be established particularly for the prenatal diagnosis of hereditary diseases and also to determine individual sensitivity to various drugs. This is usually carried out by a PCR amplification of the locus to be examined from the genomic DNA and subsequent restriction analysis or sequencing. In the first case this requires a gel electrophoretic separation of the restriction fragments which cannot be easily automated. This also applies to the second case provided a chip sequencing method is not used, but this method is not yet fully developed. The DNA fragments prepared according to the invention can also be used for this aspect. A prerequisite is that they have to be known, molecularly identified alleles. An anchor oligonucleotide prepared according to the invention is then constructed such that it hybridizes to a gene region which is directly in front of the mutation. Another oligonucleotide which contains one or several fluorescent labels hybridizes to the directly adjoining 3' region of the gene such that the two free ends of the anchor oligonucleotide DNA prepared according to the invention and of the fluorescent labelled oligonucleotide come to rest directly next to one another when a continuous hybrid is formed and can be ligated together. If the sequence differs at this site, the ends are not attached and thus also ligation does not take place. Instead an oligonucleotide labelled with a different fluorescence can for example bind to the corresponding mutated sequence and thus a different label is ligated to the biotinylated anchor. The fluorescent dyes that are bound in each case and thus the respective alleles are identified by laser excitation. In order to increase the sensitivity of the method according to the invention it is also possible to carry out a prior asymmetric PCR in this case which amplifies the locus to be examined. If the reaction conditions for the PCR and hybridization are uniform it is possible to determine several different alleles simultaneously from one sample.

11. Direct interaction analysis of protein arrays (LISPA™)

With the success of the human genome project one of the next problems is to classify ca. 50,000 genes. It is necessary not only in basic research but also in the rapidly developing field of molecular medicine to understand what these genes do, how they cooperate with one another and in which situations, which proteins, peptides or low-molecular substances bind to which other proteins etc. A first indication of such cooperations between proteins is usually a direct physical contact of the respective gene products. In order to examine such links in vitro at the protein level, one usually requires purified protein preparations. However, with 50,000 proteins this is difficult to accomplish. Therefore one usually utilizes genetic methods such as the so-called yeast two hybrid screen to identify potential interaction partners. Although this method has previously been very successfully used, it is nevertheless extremely susceptible to artifacts, laborious and unsuitable for the complexity of the present problem. This object can be achieved with a combination of the method according to the invention, the Sloning™ method and the EASYPRO™ method according to the invention in combination with a biochip. An automated method can be used to synthesize and express the complete 50,000 genes and provide them with a suitable tag for immobilization in reaction chambers of a biochip. A quantity of $10^7$ to $10^8$ molecules is usually sufficient for binding studies with a fluorescent labelled protein or a low-molecular compound. About 1 nanolitre of a protein solution can be deposited in wells of 100× 200×60 μm which corresponds to a 100 kD protein and a concentration of 5 mg/ml, ca. $3×10^{10}$ molecules. If one assumes that the actual binding capacity per well is ca. 1% of this value, sufficient material is still present even in the case of relatively large proteins. If the space between the individual wells is ca. 30 μm, the entire library of 50,000 proteins can be accommodated on a chip of only 20 cm². A laser measures the fluorescence in all wells before and after binding the fluorescent labelled target molecule from which the strength of the interaction is calculated. Wells in which only the tag is presented serve as an unspecific control. Such protein arrays can be used, for example, to detect previously undetectable drug binding to cellular proteins and to understand complicated signal transduction cascades.

12. Parallel Analysis of mRNAs Using Immobilized Nucleic Acid Arrays (PAMINA™)

One of the focuses of modern drug research is to selectively manipulate the expression of individual genes. For this purpose it is necessary to examine as extensively as possible the influence of new active substances on the expression of other genes. In signal transduction processes, cell differentiation or in the case of disease-induced metabolic changes an entire cascade of different genes is often switched on or off. However, due to the complexity of gene expression in higher organisms it has hitherto been impossible to simultaneously analyse more than a handful of genes. However, the sequencing of the human genome provides the future basis for a comprehensive parallel analysis of the entire gene expression of a cell. From the available sequence information it is possible to use computerized sequence comparisons to firstly identify the regions in the individual genes which have the lowest homology to one another i.e. the highest degree of specificity for the respective gene. Gene-specific single-stranded antisense anchor DNAs can be derived from these gene sections which are then immobilized in an array on a biochip. The antisense anchor DNAs can be designed such that the melting temperatures of all RNA/DNA hybrids are within a narrow range. Hybridization of the entire RNA or of the polyA+-RNA of the cells to be examined to this array under conditions of maximum stringency generates RNA/DNA hybrids in each well of the biochip if the corresponding mRNA is expressed. The immobilized antisense anchor DNAs are elongated in a $2^{nd}$ step on the hybridized RNA template by treatment with an RNaseH reverse transcriptase and modified nucleotides which are preferably fluorescent labelled. After several washing processes to separate non-incorporated nucleotides, the cDNA reaction products can be measured in a similar manner to the described LISPA™ technique by laser scanning of the individual wells.

Examples of Application

1. Production of the Anchor and Splinker Oligonucleotides

The anchor and splinker oligonucleotides were prepared according to the standard method described by Sinha N. D., Biernat J., McManus J., Köster H., *Nucleic Acids Res,* 1984 June, 12:11, 4539-57 or by a synthesis on a large scale which was subsequently quartered or by simultaneous synthesis on cellulose membranes.

2. Labelling with a Modification

The oligonucleotides were modified by standard methods.

3. Coupling to the Matrix 20-200 pmol biotin-labelled kinase-treated anchor oligonucleotides were added to 10 µl streptavidin-coupled magnetized beads (MERCK) in a total volume of 50 µl in 1×TE/1 M NaCl, pH 7.5 and incubated for 30 min at room temperature on a roller. Subsequently non-bound anchor oligonucleotides were washed away by a three-fold buffer change of 500 µl 1×TE, pH 7.5 each time.

4. First Ligation Step

The ligation was carried out at 4° C., 16° C., room temperature or 37° C. (standard 16° C.) in a volume of 50 µl in 1× ligase buffer (Boehringer Mannheim) containing 1 to 5 units T4 DNA ligase (Boehringer Mannheim or New England Biolabs) for 15 to 60 minutes. 20 pmol phosphorylated anchor oligonucleotide was usually used for the ligation. Splinker oligonucleotides phosphorylated at the 5' end were added in a 1.5 to 5-fold molar excess. After the reaction, ligase and non-ligated splinker oligonucleotides were washed away by a three-fold buffer change of 500 µl 1×TE, pH 7.5 each time. Afterwards 40 µl of a restriction mix which contained the splinker-specific restriction enzyme Eco31I in 1.25×restriction buffer (buffer A from Boehringer Mannheim or buffer 4 from New England Biolabs) was added to the washed beads. Subsequently they were washed as described above.

5. Second Ligation Step

Four further ligations were carried out with other splinker oligonucleotides according to the protocol described in section 4.

6. Transposition

After the $5^{th}$ ligation a mix of the anchor-specific restriction enzyme Esp3I or BpiI in the appropriate manufacturer-specific buffers was added after washing and incubated for 30 to 60 minutes at 37° C. After the reaction the complete mix including the cleaved ligated splinker oligonucleotides was removed, heat-treated in a separate reaction vessel for 15 minutes at 65° C. in order to inactivate the restriction enzyme and then ligated in another reaction vessel with appropriately ligated anchor oligonucleotides coupled to magnetized streptavidin beads.

7. Restriction Control of Ligated Fragments

In order to monitor the correct size of the cleaved splinker oligonucleotides a 5 µl aliquot of the reaction mixture was separated on an 18% 1×TBE polyacrylamide gel, stained for 10 minutes with 0.01% SYBR-Gold™ in 1×TBE and visualized with UV light. Length differences of 1-2 bases can be detected on such a gel.

The invention claimed is:

1. A method for producing a synthesized nucleic acid molecule comprising the steps of:
(a) providing a double-stranded first oligonucleotide which is prepared by the following steps:
aa) coupling one end of a first modified oligonucleotide comprising a double-stranded nucleic acid to a surface of a first solid matrix wherein the first modified oligonucleotide contains a recognition sequence for a first type IIS restriction enzyme which cleaves the downstream sequence of the recognition sequence in the first modified oligonucleotide,
ab) providing a double-stranded second oligonucleotide that is different from the first modified oligonucleotide of step aa), wherein the second oligonucleotide is partially self-complementary, and contains a loop and a recognition sequence for a second type IIS restriction enzyme which cleaves the downstream sequence of the recognition sequence in the second oligonucleotide, wherein the recognition sequence of the first type II restriction enzyme in the first modified oligonucleotide and the recognition sequence of the second type IIS restriction enzyme in the second oligonucleotide are different,
ac) ligating the first modified oligonucleotide on the surface of the first solid matrix and the second oligonucleotide from steps aa) and ab) and forming a first ligation product,
ad) removing the first modified oligonucleotide and the second oligonucleotide from steps aa) and ac) that are not coupled or ligated,
ae) cleaving the first ligation product obtained from step ad) with the second type IIS restriction enzyme whereby the cleavage occurs in the nucleic acid sequence of the second oligonucleotide of the first ligation product and resulting in a first elongated oligonucleotide comprising the recognition sequence of the first type IIS restriction enzyme and a first shorter oligonucleotide, wherein the first ligation product from step ac) is double-stranded,
af) separating the second type IIS restriction enzyme and the first shorter oligonucleotide from the first elongated oligonucleotide obtained in step ae),
ag) providing a double-stranded third oligonucleotide that is different from the first elongated oligonucleotide, wherein the third oligonucleotide is partially self-complementary, and contains a loop and a recognition sequence for a third type IIS restriction enzyme which cleaves the downstream sequence of the recognition sequence in the third oligonucleotide, wherein the recognition sequence for the first type IIS restriction enzyme in the elongated oligonucleotide and the recognition sequence for the third type IIS restriction enzyme in the third oligonucleotide are different,
ah) ligating the first elongated oligonucleotide obtained from steps af) and the third oligonucleotide of step ag) and forming a second ligation product,
ai) removing the first elongated oligonucleotide and the third oligonucleotide from step ah) that are not ligated,
aj) cleaving the second ligation product obtained from step ai) with the third type IIS restriction enzyme whereby the cleavage occurs in the nucleic acid sequence of the third oligonucleotide of the second ligation product and resulting in a second elongated oligonucleotide comprising the recognition sequence of the first type IIS restriction enzyme and a second shorter oligonucleotide, wherein the second ligation product from step ah) is double-stranded,
ak) separating the third type IIS restriction enzyme and the second shorter oligonucleotide from the second elongated oligonucleotide obtained in step aj), wherein the second elongated oligonucleotide is the first oligonucleotide;
(b) providing a double-stranded fourth oligonucleotide which is prepared by the following steps:
ba) coupling one end of a second modified oligonucleotide comprising a double-stranded nucleic acid to a surface of a second solid matrix wherein the second modified oligonucleotide contains a recognition sequence for a fourth type IIS restriction enzyme which cleaves the downstream sequence of the recognition sequence in the second modified oligonucleotide,
bb) providing a double-stranded fifth oligonucleotide that is different from the second modified oligonucleotide of step ba), wherein the fifth oligonucleotide is partially self-complementary, and contains a loop and a recognition sequence for a fifth type IIS restriction enzyme which cleaves the downstream sequence of the recognition sequence in the fifth oligonucleotide, wherein the recognition sequence for the fourth type IIS restriction enzyme in the second modified oligonucleotide and the recognition sequence for the fifth type IIS restriction enzyme in the fifth oligonucleotide are different,
bc) ligating the second modified oligonucleotide on the surface of the second solid matrix and the fifth oligonucleotide from steps ba) and bb) and forming a third ligation product,
bd) removing the second modified oligonucleotide and the fifth oligonucleotide from steps ba) and bc) that are not coupled or ligated,
be) cleaving the third ligation product obtained from step bd) with the fifth type IIS restriction enzyme whereby the cleavage occurs in the fifth oligonucleotide of the third ligation product and resulting in a third elongated oligonucleotide comprising the recognition sequence of the fourth type IIS restriction enzyme and a third shorter oligonucleotide, wherein the third ligation product from step bc) is double-stranded,
bf) separating the fifth type IIS restriction enzyme and the third shorter oligonucleotide from the third elongated oligonucleotide obtained in step be),
bg) providing a double-stranded sixth oligonucleotide that is different from the third elongated oligonucleotide, wherein the sixth oligonucleotide is partially self-complementary, and contains a loop and a recognition sequence for a sixth type IIS restriction enzyme which cleaves the downstream sequence of the recognition sequence in the sixth oligonucleotide, wherein the recognition sequence for the fourth type IIS restriction enzyme in the third elongated oligonucleotide and the recognition sequence for the sixth type IIS restriction enzyme in the sixth oligonucleotide are different,
bh) ligating the third elongated oligonucleotide obtained from step bf) and the sixth oligonucleotide of step bg) and forming a fourth ligation product,
bi) removing the third elongated oligonucleotide and the sixth oligonucleotide from step bh) that are not ligated,
bj) cleaving the fourth ligation product obtained from step bi) with the sixth type IIS restriction enzyme whereby the cleavage occurs in the sixth oligonucleotide of the fourth ligation product and resulting in a fourth elongated oligonucleotide comprising the recognition sequence of the fourth type IIS restriction enzyme and a fourth shorter oligonucleotide, wherein the fourth ligation product from step bh) is double-stranded, bk) separating the sixth type IIS restriction enzyme and the fourth shorter oligonucleotide from the fourth elongated oligonucleotide obtained in step bj), wherein the fourth elongated oligonucleotide is the fourth oligonucleotide;

(c) ligating the first oligonucleotide and the fourth oligonucleotide from steps (a) and (b) and forming a fifth ligation product, (d) removing the first oligonucleotide and the fourth oligonucleotide from step (c) that are not ligated;

(e) cleaving the fifth ligation product obtained from step (d) with the first type IIS restriction enzyme or the fourth type IIS restriction enzyme, and resulting in a fifth elongated oligonucleotide and a fifth shorter oligonucleotide, wherein the fifth ligation product from step (c) is double-stranded; and (f) separating and removing the first type IIS restriction enzyme or the fourth type IIS restriction enzyme and the fifth shorter oligonucleotide from the fifth elongated oligonucleotide obtained from step (e), wherein the fifth elongated oligonucleotide is retained, wherein the synthesized nucleic acid molecule is the fifth elongated oligonucleotide.

2. The method of claim 1, wherein further comprises performing an exonuclease and/or phosphatase reaction/reactions after step ac), bc), or (c).

3. The method of claim 2, wherein unreacted exonuclease and/or phosphatase are removed after the exonuclease and/or phosphatase reaction/reactions.

4. The method of claim 1, wherein the end of the first modified oligonucleotide from step aa) or the second modified oligonucleotide ba) that is not coupled to the surface of the first solid matrix or the second solid matrix contains a first part of a recognition sequence for a seventh type IIS restriction enzyme, and wherein the second oligonucleotide from step ab) or the fifth oligonucleotide from step bb) contains the second part of the recognition sequence for the seventh type IIS restriction enzyme.

5. The method of claim 1, wherein each of the first modified oligonucleotide and the second modified oligonucleotide comprises biotin, digoxigenin, fluorescein isothiocyanate, an amino compound or a succinyl ester.

6. The method as claimed in claim 1, wherein the first modified oligonucleotide from step aa) or the first oligonucleotide from step (a) and/or the second modified oligonucleotide from step ab) or the fourth oligonucleotide from step (b) have/has a loop.

7. The method of claim 6, wherein the loop of the first modified oligonucleotide from step aa) or the second modified oligonucleotide from step ba) comprises a modification.

8. The method of claim 1, wherein each of the first solid matrix and the second solid matrix is selected from the group consisting of a bead, a microscope slide, a DNA chip, a well of a microtitre plate and a test tube.

9. The method of claim 8, wherein each of the first solid matrix and the second solid matrix is a bead and said bead is made of a material selected from the group consisting of glass and polystyrene.

10. The method of claim 1, wherein each of the first solid matrix and the second solid matrix comprises streptavidin, an anti-digoxigenin antibody, or an anti-fluorescein isothiocyanate antibody.

11. The method of claim 1, wherein the end of the first modified oligonucleotide from step aa) or the end of the second modified oligonucleotide from step ba) that is not coupled to the surface of the first solid matrix or the second solid matrix has a single-stranded overhang which is mutually complementary to an end of the second oligonucleotide from step ab) or an end of the fifth oligonucleotide from step bb), and wherein the end of the first modified oligonucleotide from step aa) or the end of the second modified oligonucleotide from step ba) that is not coupled to the surface of the first solid matrix or the second solid matrix and the end of the second oligonucleotide from step ab) or the end of the fifth oligonucleotide from step bb) are ligated to each other in step ac) or bc).

12. The method of claim 11, wherein the single strand overhang is 1, 2, 3, 4, or 5 nucleotides long.

13. The method of claim 1, wherein the second oligonucleotide in step ab) or the fifth oligonucleotide in step bb) is a PCR product, a plasmid vector, a phage or viral DNA, an artificial chromosome or another synthetic DNA.

* * * * *